United States Patent
Floyd et al.

(10) Patent No.: US 7,017,413 B2
(45) Date of Patent: Mar. 28, 2006

(54) METHODS FOR QUANTITATIVELY DETERMINING LENGTHWISE SHRINKAGE IN WOOD PRODUCTS

(75) Inventors: Stanley L. Floyd, Enumclaw, WA (US); Mark A. Stanish, Seattle, WA (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

(21) Appl. No.: 10/814,767

(22) Filed: Mar. 31, 2004

(65) Prior Publication Data
US 2005/0217382 A1 Oct. 6, 2005

(51) Int. Cl.
*G01N 29/06* (2006.01)
(52) U.S. Cl. ............ 73/597; 73/601; 324/637; 324/639; 324/663
(58) Field of Classification Search .......... 73/597, 73/601, 624, 627, 628, 73, 75, 159, 160, 73/432.1; 324/637–640, 663–664, 683–684, 324/686–690; 356/364, 371, 376, 383–384, 356/445–448, 237, 239; 250/330, 338.1, 250/341.1, 340, 341.6, 341.8, 358.1, 359.1, 250/360.1; 144/356, 357, 380; 83/69–73, 83/365, 360–361, 370–371; 702/35, 38–40, 702/81, 179–180, 181, 189, 196, 126, 134, 702/135, 136, 155
See application file for complete search history.

(56) References Cited

U.S. PATENT DOCUMENTS

| 4,926,350 A | * | 5/1990 | Bechtel et al. ............ 702/36 |
| 4,941,357 A | * | 7/1990 | Schajer .................... 73/600 |
| 5,024,091 A | * | 6/1991 | Pellerin et al. ............ 73/597 |
| 5,394,097 A | * | 2/1995 | Bechtel et al. ........... 324/687 |
| 6,026,689 A |   | 2/2000 | Snyder et al. |
| 6,305,224 B1 | * | 10/2001 | Stanish et al. ............ 73/597 |
| 6,308,571 B1 | * | 10/2001 | Stanish et al. ............ 73/597 |
| 2002/0112542 A1 |  | 8/2002 | Walker |

FOREIGN PATENT DOCUMENTS

| CA | 2316046 A | * | 2/2001 |
| JP | 2000105228 A | * | 4/2000 |
| WO | WO 00/36413 | * | 6/2000 |
| WO | WO 01/77669 A1 | * | 10/2001 |

* cited by examiner

*Primary Examiner*—Hezron Williams
*Assistant Examiner*—Rose M. Miller
(74) *Attorney, Agent, or Firm*—Christensen O'Connor Johnson Kindness PLLC

(57) ABSTRACT

Embodiments of the present invention quantify lengthwise shrinkage to a higher degree of accuracy over currently known methods by employing reactive force values, such as stiffness measurements, in conjunction with motive force values, such as chemical composition, of the wood product.

21 Claims, 21 Drawing Sheets

METHODS FOR QUANTITATIVELY DETERMINING LENGTHWISE SHRINKAGE IN WOOD PRODUCTS

FIELD OF THE INVENTION

The present invention relates generally to quantifying characteristics of wood products, and more particularly, to methods for quantitatively determining lengthwise shrinkage in wood products, which may in turn, be used to determine warp potential of wood products.

BACKGROUND OF THE INVENTION

Inefficient processing of raw timber and lumber wastes tremendous forest resources. To that end, the forest products industry is always looking for the ability to effectively and economically match the lumber needs of end-users and the lumber supplier of the product. It is well known that many factors control the suitability of lumber for any particular purpose. One factor that has become an increasingly important consideration is warp stability of lumber. The presence of warp affects the grading of the lumber, and thus, the value of the lumber to the lumber supplier.

Currently known methods of predicting warp potential in wood products, such as lumber, are disclosed in U.S. Pat. Nos. 6,293,152, 6,305,224 and 6,308,571, the disclosures of which are hereby incorporated by reference. A brief discussion of one conventional method for determining warp potential in wood products will now be described with reference to FIG. 1, which illustrates a pictorial overview of such a warp potential determination method. Generally described, the warp potential determination method quantifies a lengthwise shrinkage map for a selected wood product and then quantifies the warp potential in such a wood product based on the lengthwise shrinkage map.

To quantify the lengthwise shrinkage map of the wood product, several steps typically occur. First, sound velocity measurements, which are a non-destructive way of obtaining stiffness measurements, are taken at a plurality of measuring locations along the wood product and compiled to form a sound velocity profile, as best shown in FIG. 1. One example of a sound velocity profile generated in this manner is shown in FIG. 2. The sound velocity measurements may be taken at any interval along the wood product's width and length. Next, an empirical relationship or correlation between actual lengthwise shrinkage and sound velocity for the wood product (i.e., loblolly pine lumber) is obtained. This correlation is typically obtained by conducting tests on a plurality of sample specimens that are representative of the wood product. For example, sound velocity measurements may be obtained for each specimen. Next, actual lengthwise shrinkage measurements of each specimen are obtained. This may be accomplished by measuring the specimens at an equilibrium moisture content (EMC) at a relative humidity (RH) of 90%. The specimens are then brought to an equilibrium moisture content at 20% RH and the lengthwise shrinkage measurements are repeated. After the sound velocity measurements and the actual lengthwise shrinkage measurements are obtained for each specimen, a correlation between sound velocity and lengthwise shrinkage may be determined using well-known regression techniques, such as the least squares model. One example of sound velocity-lengthwise shrinkage correlation generated in this manner is shown in FIG. 3.

Once the empirically determined, sound velocity-lengthwise shrinkage correlation is quantified, the resulting quantified correlation is utilized to convert the sound velocity profile of the wood product into a lengthwise shrinkage map. One example of a lengthwise shrinkage map generated in this manner is shown in FIG. 4. This map can then be used to determine warp potential, such as crook, of the wood product. For example, the data comprising the lengthwise shrinkage map can be entered into a computerized finite element model (FEM) to be analyzed. The finite element model simulates the stress and strain components of the wood product. One such finite element model that my be utilized is the DIMENS model developed by Weyerhaeuser Company, Federal Way, Wash. The finite element model simulation quantitatively determines the warp potential for the wood product.

Thus, the prior art method includes the steps of: (1) measuring sound velocities at a plurality of measuring locations along a selected wood product, such as a Loblolly pine board, and compiling those measurements to form a sound velocity profile; (2) correlating sound velocity to lengthwise shrinkage from a plurality of specimens representative of the wood product; (3) converting the sound velocity profile into a lengthwise shrinkage map using the sound velocity-lengthwise shrinkage correlation; and (4) quantitatively determining the warp potential for the wood product by analyzing the lengthwise shrinkage map with a computerized finite element model, such as the DIMENS model. For a more detailed description of prior art warp potential determination methods, please refer to U.S. Pat. Nos. 6,293,152, 6,305,224 and 6,308,571, the disclosures of which are hereby incorporated by reference.

According to the aforementioned methods, warp-prone wood products can now be nondestructively identified during or prior to processing and product placement, resulting in more efficient processing of raw timber and lumber into wood products. Employing these methods may allow raw logs to be culled prior to manufacturing, and wood-products manufacturing processes to be altered to direct raw lumber to various end products according to quality and value. For example, warp-prone trees can now be identified while standing in forests or after cutting, and processed into products where warp is an irrelevant consideration (e.g. paper products, chipping, etc.). Green warp-prone lumber can be identified at the mill, separated, and kiln-dried using special warp-reducing techniques (e.g. rapid-drying, high-heat drying, final steaming, restraint-drying, etc.). Lumber having low warp potential can be dried using simpler and more economical methods.

Additionally, employing the currently known methods decreases the waste of natural resources by restricting the use of certain types of wood in inappropriate applications. For example, warp-prone logs determined by those methods can now be cut into lumber with cuts being coordinated to reduce warp, or the orientation of boards taken from certain logs can be altered to reduce warp. Alternatively, warp-prone logs can now be culled and processed for specific uses (e.g. chipped, lumber for pallets, etc.). Lumber cut from warp-prone logs also can be specially processed (e.g. special kiln drying techniques) or used in selected applications (e.g. relative constant moisture applications).

Further, warp-prone lumber can be identified for restrictive use in certain applications. For example, exterior window and door casings experience fluctuating moisture and temperature conditions during use. Warp prone lumber, even if initially straight when dried, could warp in such changing environments. Thus, the use of warp-prone lumber in warp-inducing environments can be avoided. Extremely warp-prone wood may be suitable only for uses where warping is not a significant problem (e.g. for pallets, landscape applications, etc.). In such cases, warp-prone green lumber can now be processed without expensive drying techniques.

While these currently known techniques for predicting warp potential in wood products have proven to be satisfactory in increasing the efficiency of lumber processing, improvements to these methods by the forest products industry are desired.

SUMMARY OF THE INVENTION

In accordance with aspects of the present invention, a method for quantifying at least one lengthwise shrinkage of a wood product is provided. The method includes obtaining at least one first data value indicative of a reactive force component to lengthwise shrinkage. The first data value is obtained at a measuring location along the wood product. The method also includes obtaining at least one second data value indicative of a motive force component to lengthwise shrinkage. The second data value is obtained at the measuring location along the wood product. The method further includes determining lengthwise shrinkage of the wood product based on the first and second data values.

In accordance with another aspect of the present invention, a method for quantifying lengthwise shrinkage of wood products is provided. The method includes obtaining at least one resistive force component measurement; obtaining at least one driving force component measurement; obtaining a correlation between lengthwise shrinkage and both resistive force and driving force; and calculating lengthwise shrinkage in the wood product based on the correlation and the resistive force component and driving force component measurements.

In accordance with another aspect of the present invention, a method for quantifying lengthwise shrinkage of wood products is provided. The method includes obtaining a wood product; obtaining a sound velocity measurement from the wood product at a first measuring location; obtaining a galactan measurement from a wood product at the first measuring location; and determining lengthwise shrinkage of the wood product based on the sound velocity measurement and the chemical composition measurement.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENTS

Figure 1:
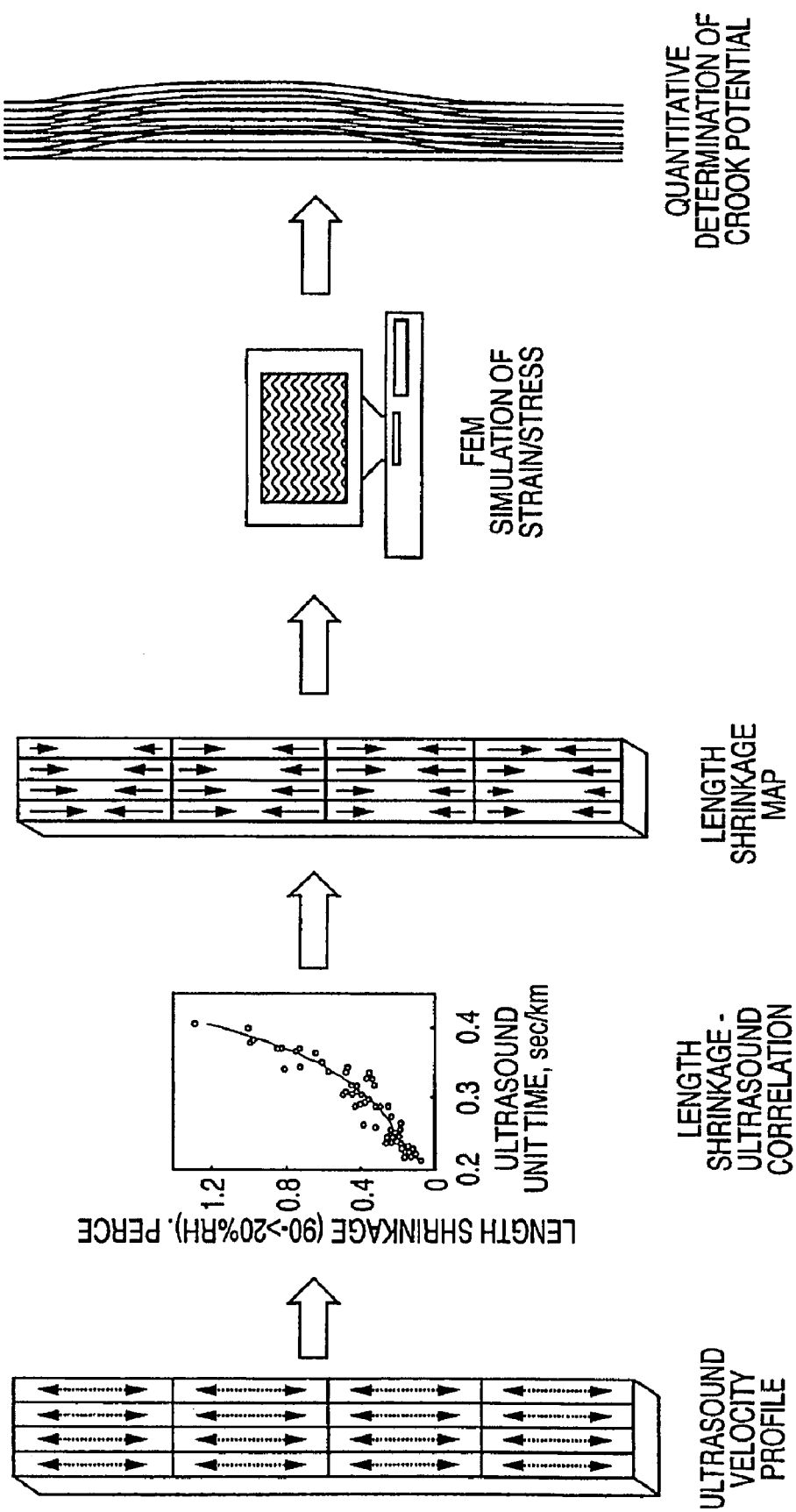
FIG. 1 is a pictorial overview of one prior art method of determining warp potential in wood products.
Figure 2:
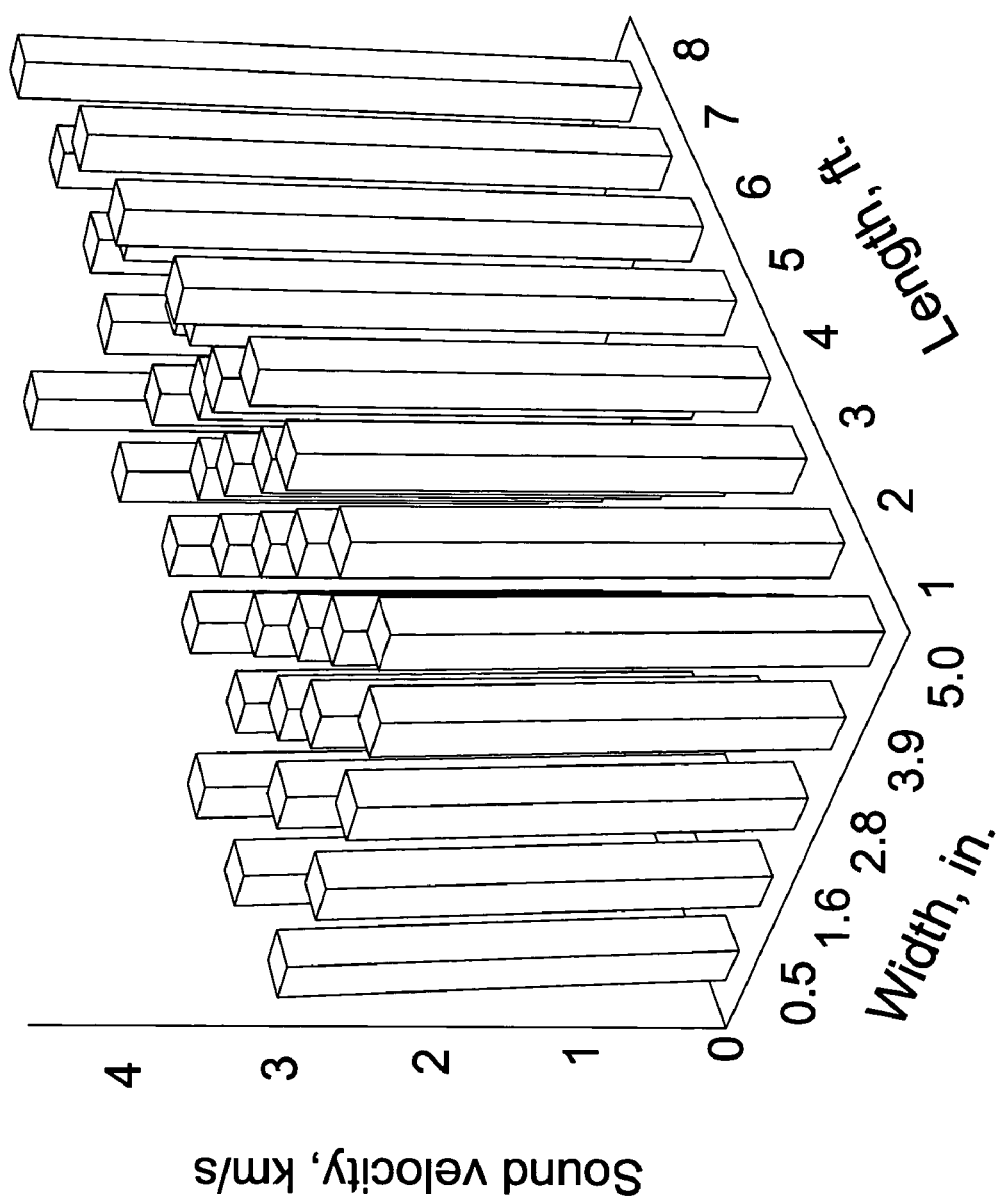
FIG. 2 is an example of a sound velocity profile of a wood product generated with the prior art method of FIG. 1.
Figure 3:
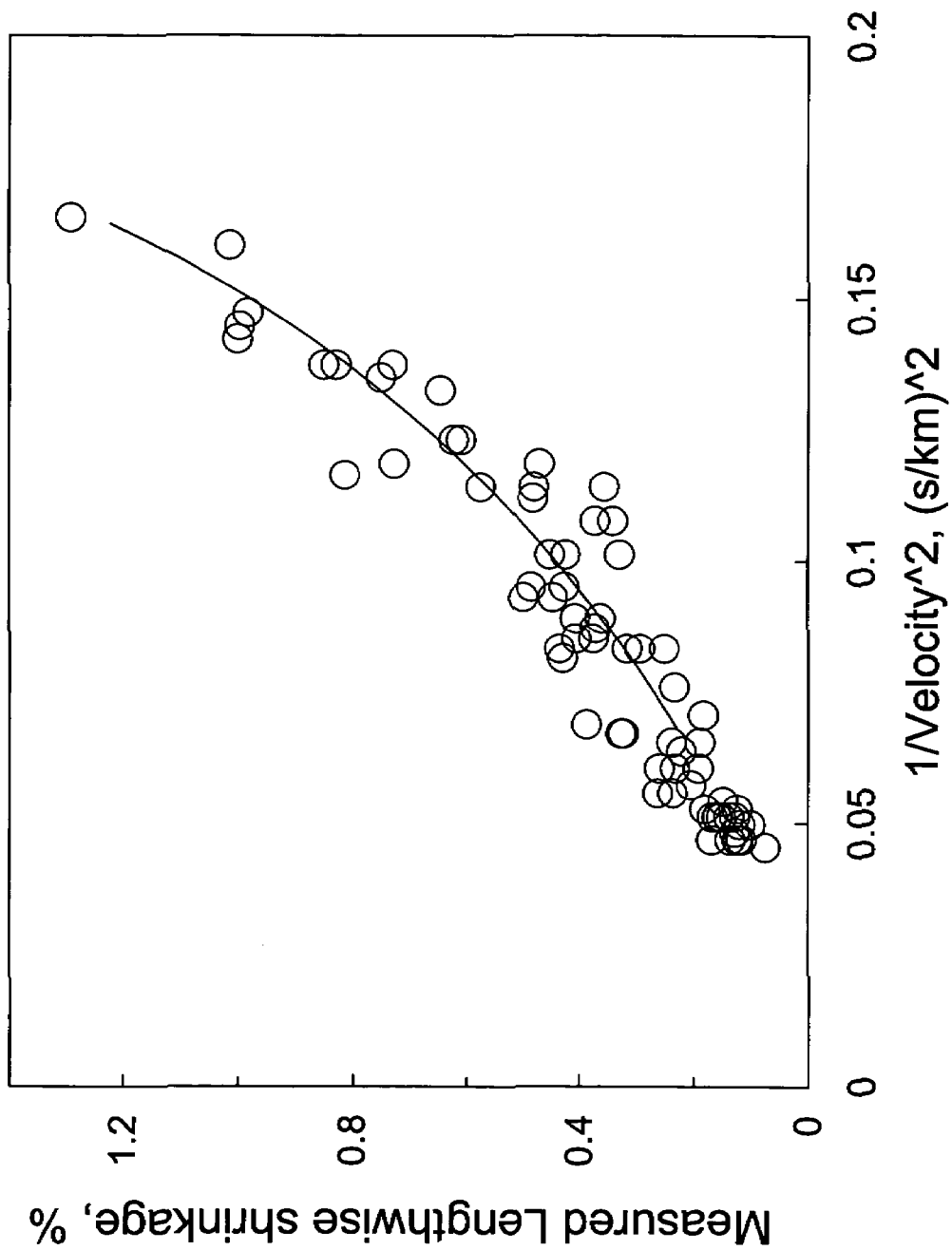
FIG. 3 is an example of a chart illustrating the correlation between sound velocity and measured lengthwise shrinkage in a wood product generated with the prior art method of FIG. 1.
Figure 4:
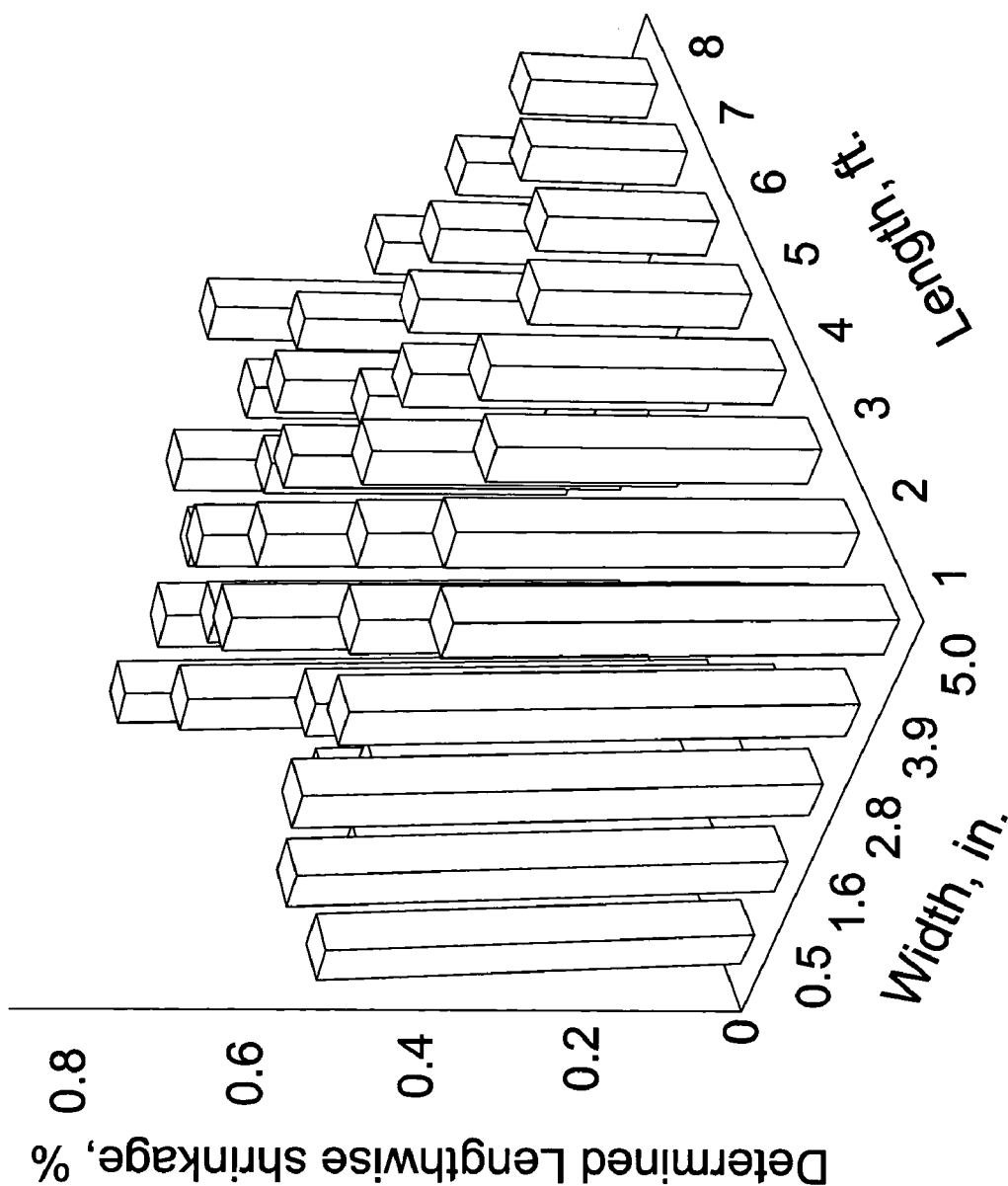
FIG. 4 is an example of a determined lengthwise shrinkage map generated with the prior art method of FIG. 1 using the information set forth in FIGS. 2 and 3.

Embodiments of the present invention will now be described with reference to the accompanying drawings where like numerals correspond to like elements. Embodiments of the present invention are directed to methods for determining lengthwise shrinkage of wood products. Specifically, embodiments of the present invention employ two correlative data values to quantitatively determine lengthwise shrinkage in wood products. By determining the lengthwise shrinkage of wood products in this manner, more accurate results may be achieved than current methods that rely solely on either acoustic energy or stiffness measurements, resulting in better utilization of the wood products and higher profitability to wood processors. The term "wood products" is used herein to refer to standing trees, raw logs soon after harvesting, processed logs awaiting milling, processed lumber (e.g.; planks, boards, and studs), manufactured wood products (e.g.; plywood, oriented strand board, fiberboard, etc.), and engineered wood products (e.g.; laminated veneer and finger jointed lumber). The methods described herein may be practiced on any type of wood, including but not limited to, hardwoods, softwoods, and combinations thereof. It will be apparent to those skilled in the art that embodiments of the present invention described herein are illustrative in nature, and should not limit the scope of the present invention, as claimed.

A. General Description of Embodiments of the Present Invention

Embodiments of the present invention are directed to methods suitable for quantifying lengthwise shrinkage in wood products, which in turn, may be used in determining warp potential in such wood products. From the discussion of the prior art method above, it was shown that the accuracy of the warp potential determination depends primarily on the accuracy of the quantitatively determined lengthwise shrinkage values. Because lengthwise shrinkage is related only approximately to sound velocity, warp potential determinations using lengthwise shrinkage based on sound velocity measurements alone, although accurate enough in some applications, may not be accurate enough for specific applications. Accordingly, embodiments of the present invention employ two factors that can be correlated to lengthwise shrinkage in wood products.

Prior to describing the various embodiments of the present invention, the basic mechanisms that determine lengthwise shrinkage will be described. To that end, lengthwise shrinkage, in general, is the local displacement that a particular segment of the wood product undergoes during drying. Displacement is generally governed by motive forces, i.e.; those forces that tend to promote shrinking, and reactive or resistive forces, i.e.; those forces that tend to resist shrinking. As such, by focusing on both the motive and reactive force components of displacement when determining lengthwise shrinkage, as opposed to only sound velocities like the prior art, embodiments of the present invention obtain more accurate results, as will be described in more detail below.

Generally described, embodiments of the present invention can quantify lengthwise shrinkage in wood products to a higher degree of accuracy over currently known methods by employing data indicative of reactive forces, such as modulus of elasticity (MOE), in conjunction with data indicative of motive forces, such as chemical composition. Specifically, the inventors of the present invention have discovered that including chemical composition data, and in particular, the hemicellulose composition data of the wood product, as being indicative of the motive forces of displacement can increase the accuracy of the quantitatively determined lengthwise shrinkage valuation of the wood product.

Figure 5:
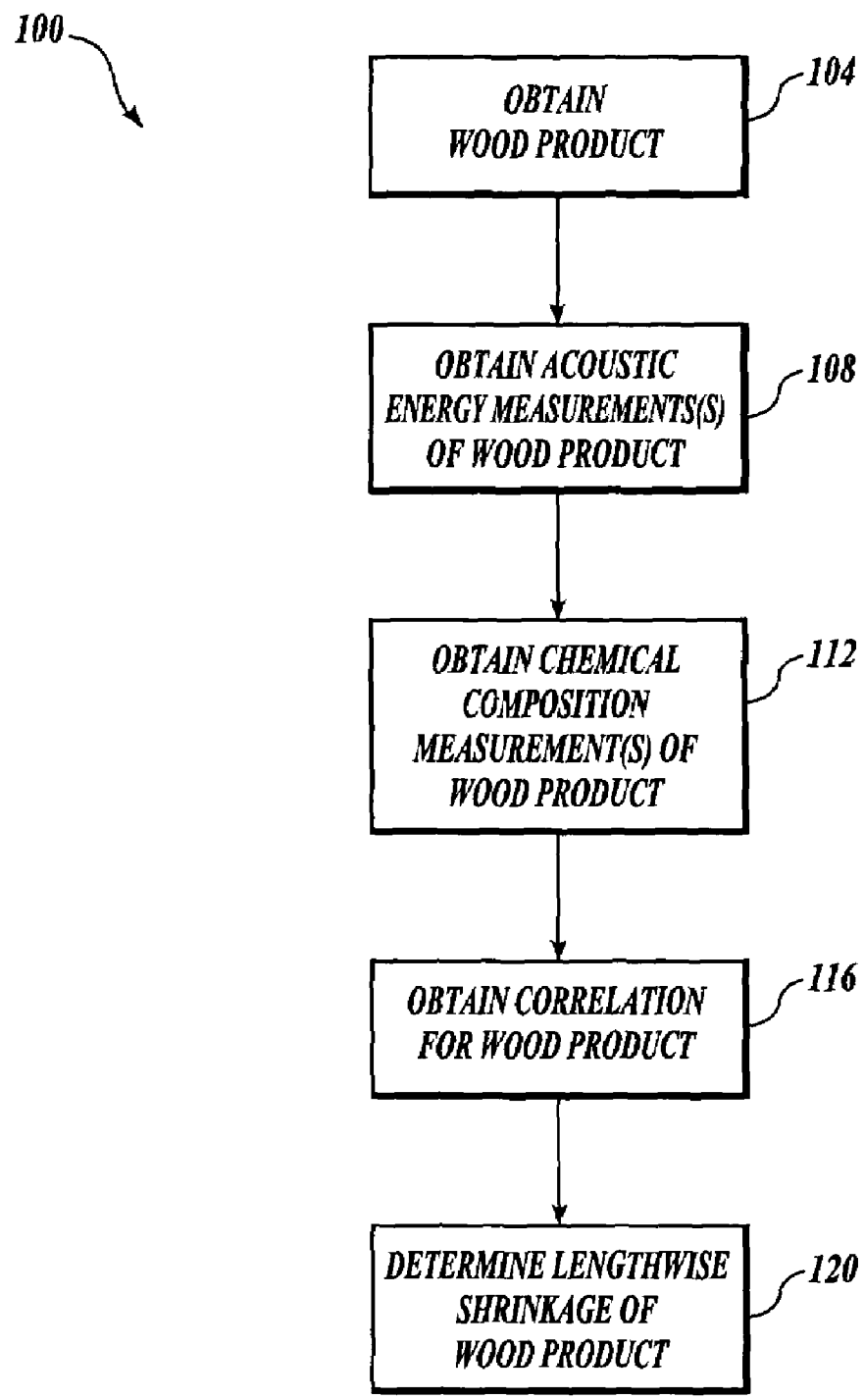
FIG. 5 is a flow chart of one method of quantitatively determining lengthwise shrinkage in a wood product in accordance with aspects of the present invention.

FIG. 5 is a flow chart of one method of the present invention, generally designated 100, that quantitatively determines lengthwise shrinkage of a wood product in accordance with aspects of the present invention. Generally described, the method begins at block 104 in which a wood product in need of warp potential determination is obtained. For example, a pruned Loblolly pine log may be selected.

Next, at block 108, at least one data value indicative of the reactive force component of displacement, is obtained. For example, it is believed by the inventors of the present invention that stiffness or Modulus of Elasticity (MOE) may be used to approximate the reactive forces. In one exemplary embodiment, the obtained data values indicative of the reactive force component are acoustic energy measurements, such as sound velocity measurements, which can approximate MOE. In several exemplary embodiments, a plurality of reactive force component measurements, such as sound velocity measurements, associated with a plurality of measuring locations along the wood product are obtained. Alternatively, in other exemplary embodiments of the present invention, the obtained data values indicative of stiffness may be obtained with conventional bending stiffness measurement equipment along a plurality of measuring locations on the wood product. It will be appreciated that either measurements may be in the form of previously obtained measurement data supplied from a third party. The measurement data may be assembled, and a data profile, such as the sound velocity profile shown in FIG. 7, may then be generated, if desired.

In exemplary embodiments of the present invention, the sound velocity measurements may be taken at intervals along the wood product's width and length using well-known sound velocity measurement equipment. For example, measurements may be taken using a commercially available Sylvatest™ apparatus, available from Sandes S A, of Granges/Vevyse, Switzerland, which measures the time-of-flight of a 14-kHz signal between handheld sender and receiver probes. Other sounding, resonating, or velocity testing devices may be utilized, so long as the signal may properly propagate through the wood product. The probes are positioned on the wood product, such as the face of a board, at predetermined distances along the wood product length, and readings of lengthwise unit travel time are taken at measuring locations across the face of the wood product and along the length of the wood product. For raw logs, the sender and receiver probes can be correspondingly located on the surface of the raw log or on the surface of the log from which a cant has been removed. Such measurements also can be taken along the lengths of standing trees, if desired. For ease of use, all sound velocity measurements discussed herein were performed with the testing device at a single frequency of detection. However, multiple frequency testing could also be performed. A more detailed description of the techniques of measuring sound velocity through wood is discussed below under the section heading "Acoustic Energy."

Once the at least one data value indicative of the reactive force component is obtained, the method proceeds to block 112, where the at least one data value indicative of the motive force component of the displacement is obtained. At least one, and in some embodiments, a plurality of motive force component data values may be obtained from the same measuring locations along the wood product's width and length as those associated with the reactive force component data values. For example, it is believed by the inventors of the present invention that chemical composition may be used to approximate the motive force component of displacement. In several exemplary embodiments of the present invention, a sample of the wood product is taken at each measuring location and is analyzed for its chemical composition, more particularly, for its hemicellulose content. In several exemplary embodiments of the present invention, the galactan content of the hemicellulose is measured, and employed to determine lengthwise shrinkage. For example, in some exemplary embodiments, the quantity of the galactan content of the hemicellulose may be used, while in other exemplary embodiments, a ratio of the quantity of galactan to the quantity of glucan (i.e. galactan/glucan ratio) may be employed. The data values obtained from the motive force component measurements, for example, chemical composition measurements, may be assembled and then may be used to generate a motive force component data profile, such as a chemical composition profile similar to the sound velocity profile of FIG. 7, if desired. A more detailed description of one technique suitable for measuring the chemical composition of the wood product is discussed below under the section heading "Chemical Composition."

Next, an empirical relationship or correlation between lengthwise shrinkage and both reactive forces and the motive forces for the wood product is obtained at block 116. This correlation may be obtained from historical test data on common wood species, such as Loblolly pine, and cataloged by wood characteristics, such as age, region (e.g., midsouth, etc.), to name a few. The historical data may be supplied by third parties for processing, or the historical data may have been already processed and supplied as a requested relationship or correlation equation. The correlation may also be obtained by conducting new tests on a plurality of sample specimens representative of the wood product. In either case, the methodology is the same. In one exemplary method of obtaining such a correction, a reactive force component measurements, for example, a sound velocity measurement are first taken for each specimen, followed by a motive force component measurement, for example, a chemical composition measurement for each specimen. Next, actual lengthwise shrinkage of each specimen is measured. This may be accomplished by first measuring the specimens at an equilibrium moisture content (EMC) at a relative humidity (RH) of 90 percent, lowering the relative humidity of the specimens to 20 percent, and then repeating the measurements on the specimens at the relative humidity (RH) of 20 percent. After the reactive force component measurement (e.g.; sound velocity measurement), the motive force component measurement (e.g. chemical composition measurement), and the actual lengthwise shrinkage value for each specimen are obtained, a correlation between lengthwise shrinkage and both reactive and motive force may be determined using well known multi-variable regression techniques, such as the least squares model.

Once the empirically determined, reactive force-motive force-lengthwise shrinkage correlation is quantified, the method proceeds to block 120, where the resulting correlation may be used to convert the assembled reactive force component measurements and motive force component measurements and/or the respective profiles, if generated, of the wood product into a lengthwise shrinkage map. For example, the assembled sound velocity and chemical composition measurements may be converted with the previously obtained sound velocity-chemical composition-lengthwise shrinkage correlation described above.

It will be appreciated that the reactive force component measurements, motive force component measurements, and the reactive force-motive force-lengthwise shrinkage correlation may be obtained in any order when practicing embodiments of the present invention, and therefore, the aforementioned example is only illustrative in nature, and should not be construed as limiting.

The following examples support the conclusion that in wood products, a warp potential determination based on sound velocity-derived lengthwise shrinkage valuations can be significantly improved by quantifying the lengthwise shrinkage characteristics with greater accuracy. Specifically, lengthwise shrinkage based on sound velocity alone can be improved using information about both reactive forces and motive forces.

EXAMPLE 1

Figure 6:
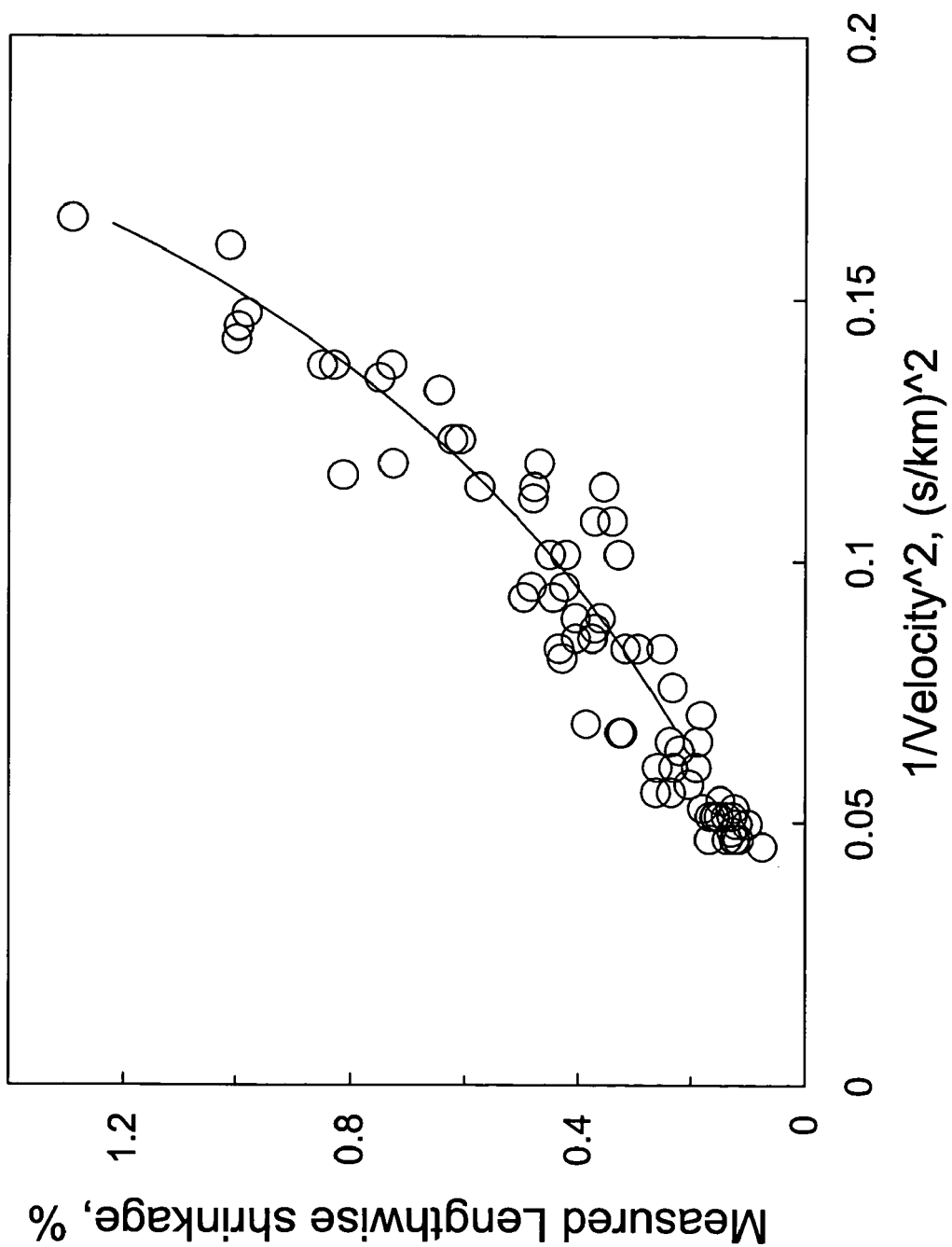
FIG. 6 is a chart illustrating the correlation between sound velocity and measured lengthwise shrinkage of multiple 1-foot-long shrinkage specimens cut from lumber sawn from the butt logs of pruned, 24-year-old loblolly pine trees.

Multiple 1-foot-long shrinkage specimens were cut from lumber sawn from the butt logs of pruned, 24-year-old loblolly pine trees. Sound velocities (at an EMC at 65% RH) and actual lengthwise shrinkage were measured for each specimen, and based on those measurements, a sound velocity-lengthwise shrinkage correlation was determined using a least squares regression model. FIG. 6 shows the relationship between lengthwise shrinkage and sound velocity for those specimens. Fourteen other boards sawn from the butt logs of the pruned, 24-year-old loblolly pine trees, each having dimensions 1×6 and 8 ft. in length, were then selected and brought to an equilibrium moisture content at 65% RH. At that condition, sound velocities were measured on the top face of each board, along 1-ft. spans parallel to the board. These sound velocity measurements were made at five locations spaced equally across the face, and repeated every foot along the board's length. Results of these measurements for one of the 14 boards is shown as a sound velocity profile in FIG. 7. The 14 boards were then brought to an equilibrium moisture content at 90% RH and the warp profile, such as crook, of each board was measured. Finally, the boards were brought to an equilibrium moisture content at 20% RH and the warp measurements were repeated.

Figure 7:
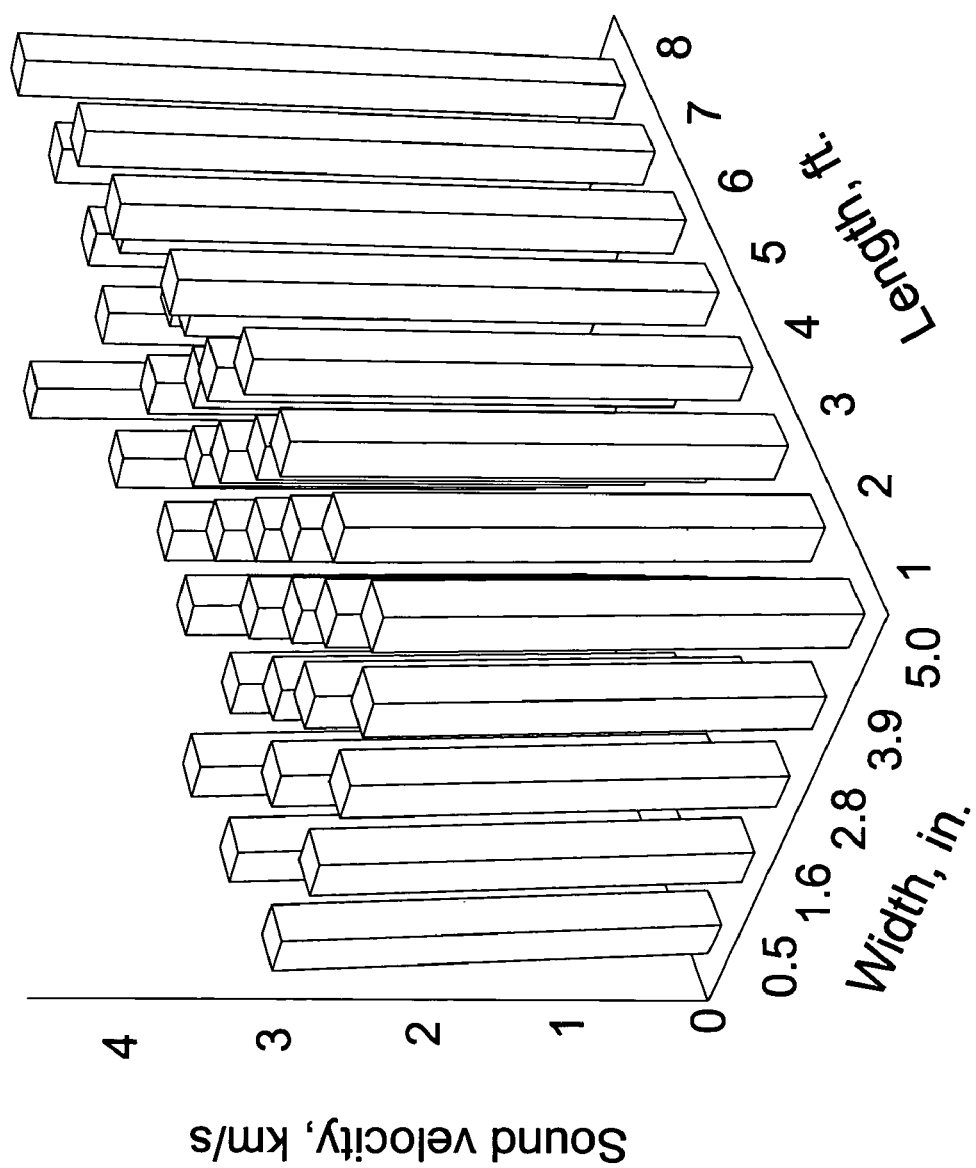
FIG. 7 is a sound velocity profile of one of the 14 boards selected from the butt logs of pruned, 24-year-old loblolly pine trees.
Figure 8:
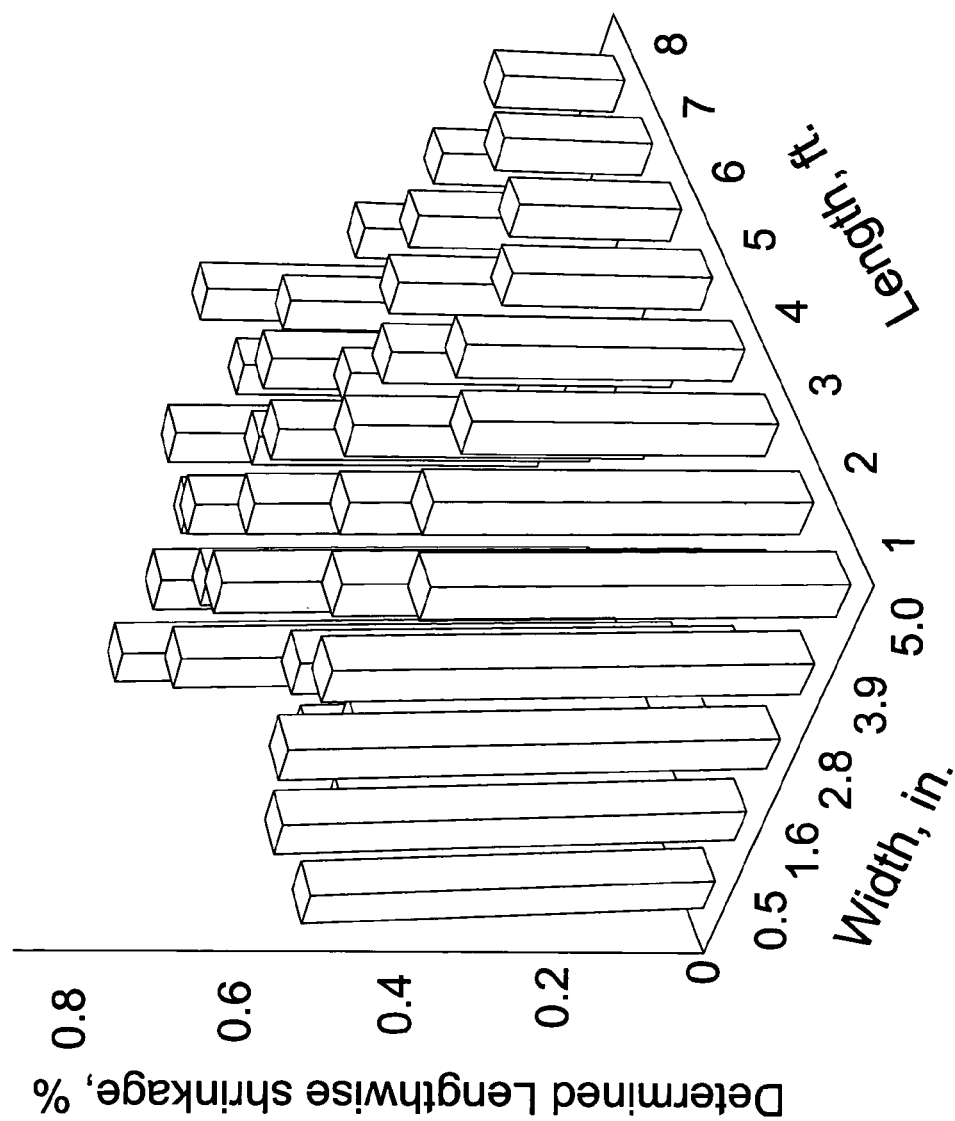
FIG. 8 is a determined lengthwise shrinkage map generated from the sound velocity profile of FIG. 7 and the correlation of FIG. 6.
Figure 9:
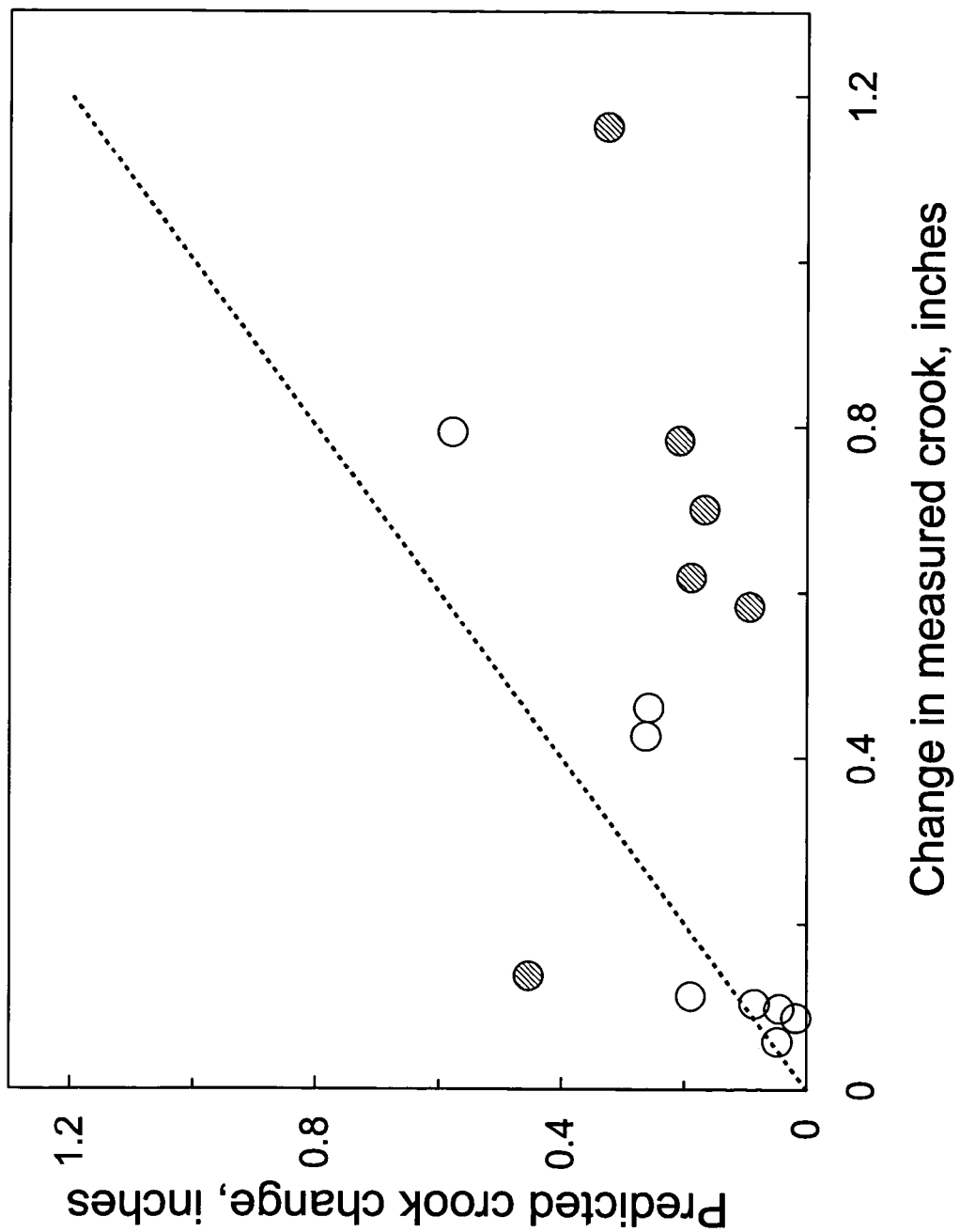
FIG. 9 is a chart illustrating a comparison of predicted crook change versus measured crook change for the 14 boards selected from the butt logs of pruned, 24-year-old loblolly pine trees.

Next, the sound velocity measurements of the board represented in FIG. 7 was converted into a lengthwise shrinkage map, which is shown in FIG. 8, using the empirical relationship between lengthwise shrinkage and sound velocity indicated by the solid line in FIG. 6. The step was then repeated for all 14 boards. The resulting lengthwise shrinkage maps were then used to predict the change in warp, such as crook, between the 90% RH and 20% RH equilibrium-moisture conditions using a finite element model, such as DIMENS. FIG. 9 compares the predicted warp change determined by DIMENS based on the quantified lengthwise shrinkage valuation to the measured (i.e., actual) warp change for all 14 boards.

Figure 10:
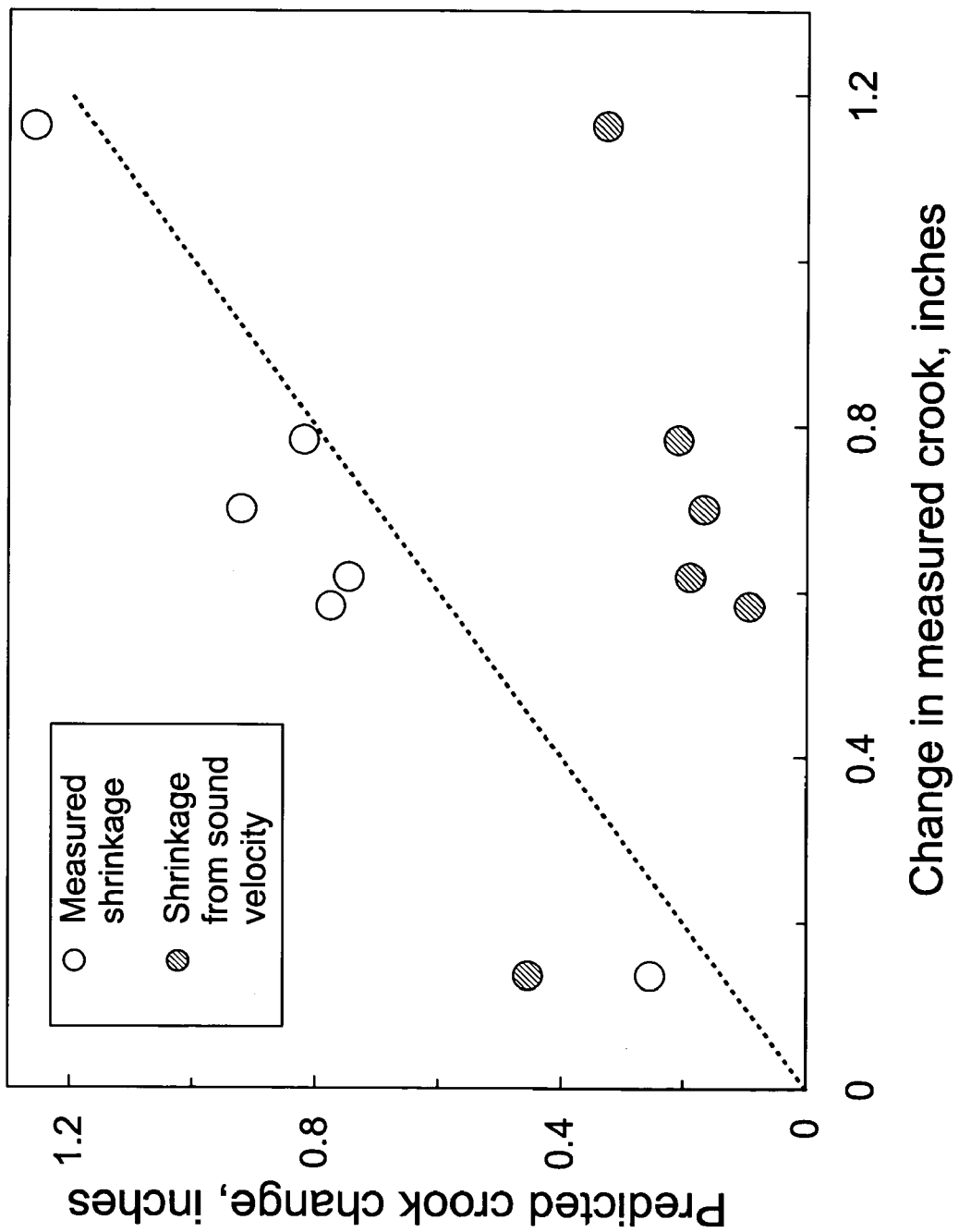
FIG. 10 is a chart illustrating the crook change predicted using both measured shrinkage values and the shrinkage valuation derived from sound velocity measurements versus measured crook change for the boards indicated by the shaded data points in FIG. 9.

Six of the boards with poorer agreement between predicted and measured warp change (those corresponding to the shaded data points in FIG. 9) were selected for further study. Each of the six selected boards were cross-cut into eight 1-foot lengths and further ripped into either three or four shrinkage specimens of equal width. The lengthwise shrinkage of these specimens were measured between the 90% RH and 20% RH equilibrium-moisture conditions, and those measured shrinkage values were used to predict the change in warp of each of the six original parent boards between the same equilibrium-moisture conditions. The warp change predicted using measured lengthwise shrinkage values and the warp change predicted using lengthwise shrinkage valuations derived from sound velocity measurements only were compared to the actual, measured warp change in FIG. 10. As can be seen in FIG. 10, for each of these six boards, the warp change prediction based on measured lengthwise shrinkage values is much closer to the actual measured warp change than is the prediction based on sound velocity-derived lengthwise shrinkage valuations alone.

Figure 11:
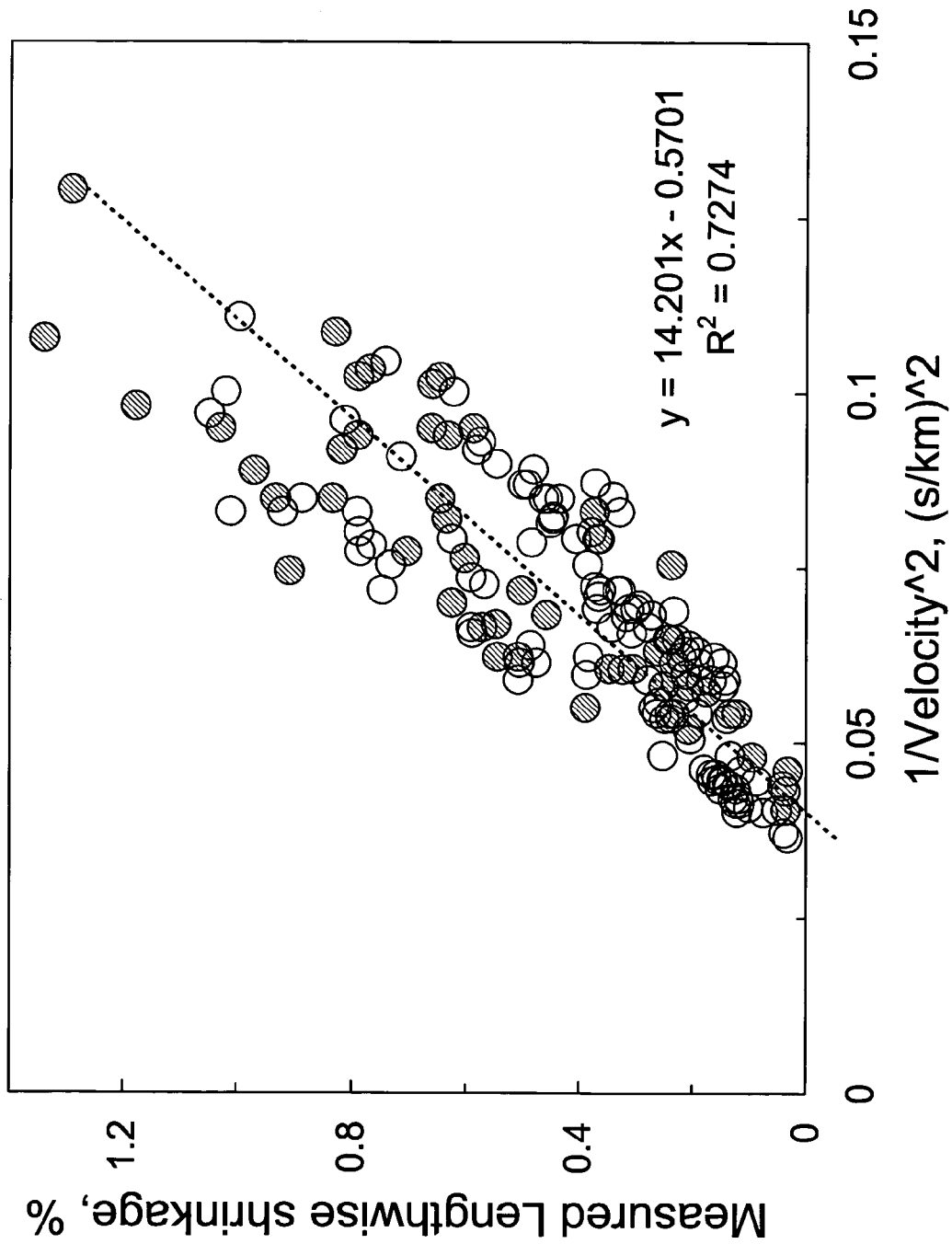
FIG. 11 is a chart illustrating the correlation between actual, measured lengthwise shrinkage and sound velocity for 64 specimens (shown by the shaded data points) created from the boards indicated by the shaded data points in FIG. 9.
Figure 12:
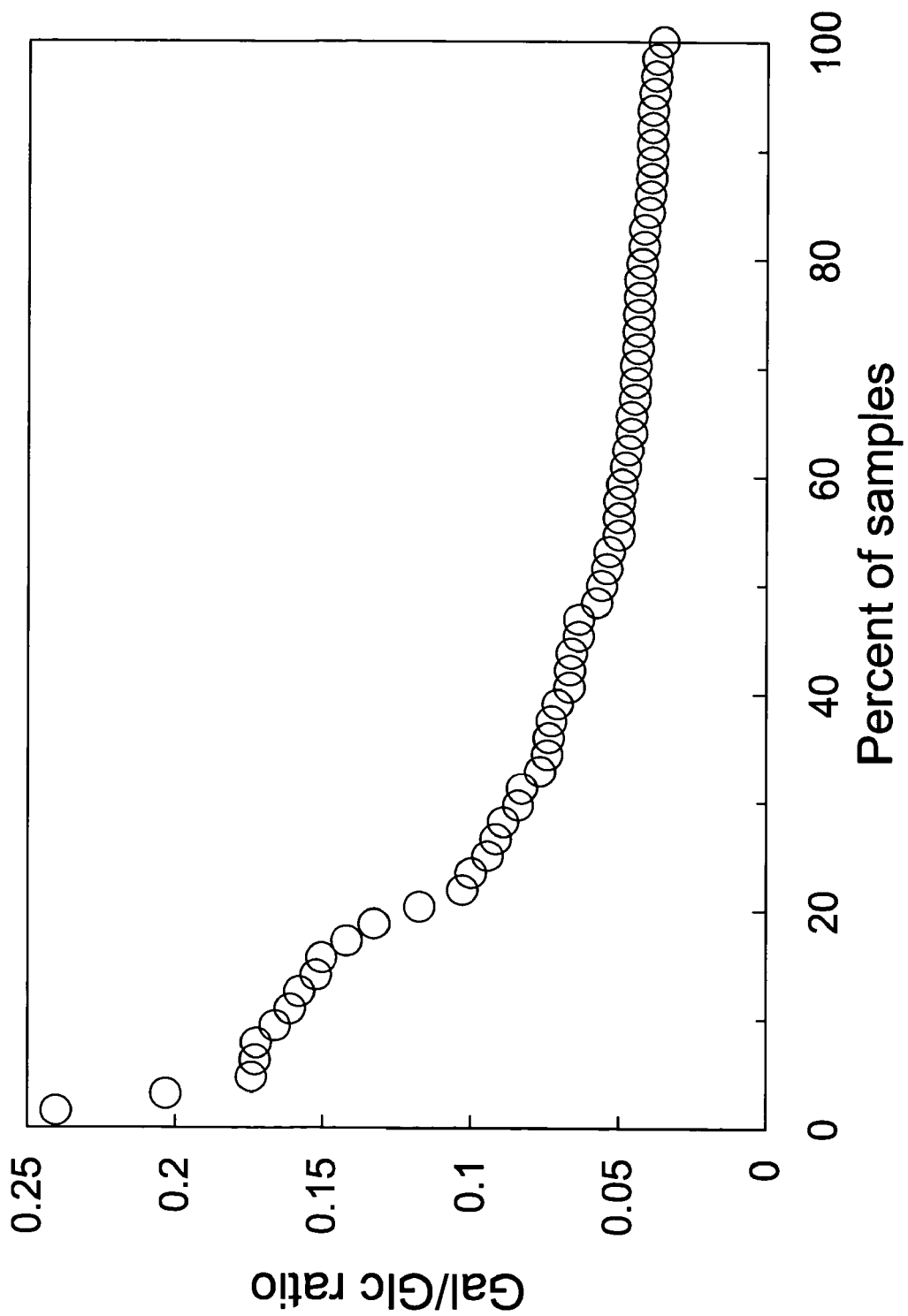
FIG. 12 is a chart illustrating the galactan content of the 64 specimens indicated by the shaded data points in FIG. 11.

Next, the chemical composition of a selected subset of the specimens ripped from the six selected boards was obtained. Specifically, the galactan content was measured for a 64-specimen subset (indicated by the shaded points in FIG. 11) of the shrinkage specimens ripped from the six selected boards. The distribution of galactan content among these specimens is displayed in FIG. 12. As can be seen in FIG. 12, about half of these specimens have a ratio of galactan to glucan (Gal/Glc ratio) that was less than 0.05, which is characteristic of normal wood. At the other extreme, the values ranged up to almost 0.25, which is more typical of compression wood.

Figure 13:
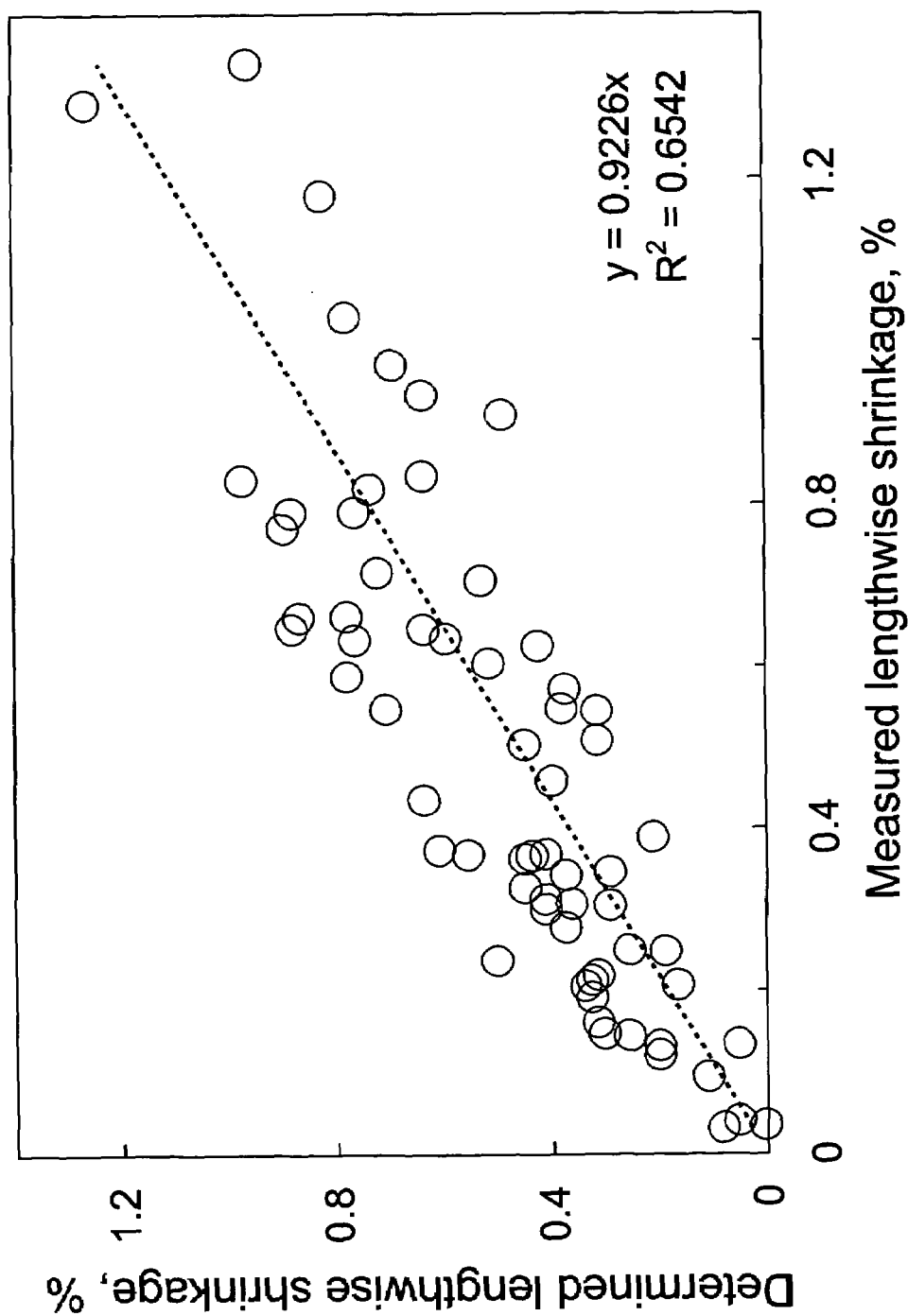
FIG. 13 is a chart illustrating the comparison of actual, measured lengthwise shrinkage and determined lengthwise shrinkage using the correlation shown in FIG. 11 for the 64 specimens indicated by the shaded data points in FIG. 11.

Sound velocity of each specimen was measured again, this time at an equilibrium moisture content at 20% RH, and a sound velocity-lengthwise shrinkage correlation was determined using the actual, measured lengthwise shrinkage values obtained earlier. The results for these 64 specimens in a single-variable least-squares correlation between lengthwise shrinkage and sound velocity includes an $R^2$ value of 0.73, the correlation being represented by the broken line in FIG. 11. Using this 64 specimen correlation as a model, a lengthwise shrinkage valuation for each specimen was determined from the sound velocity measurement of each specimen, and the results were compared to the measured lengthwise shrinkage values of each specimen previously obtained. Results of this comparison are shown in FIG. 13.

Next, a sound velocity-chemical composition-lengthwise shrinkage correlation was determined from the data obtained by measuring the sound velocity, chemical composition, and actual lengthwise shrinkage of the 64 specimens using a multi-variable least-squares regression model. Results of the two-variable least-squares correlation between lengthwise shrinkage and both sound velocity and chemical composition includes an $R^2$ value of 0.89 and then follows equation:

$$DLS = 12.93*(A) + 2.63*(B) - 0.63, \text{ wherein} \quad (1)$$

DLS=Determined lengthwise shrinkage;
A=Sound Velocity Value; and
B=Chemical Composition Value.

Figure 14:
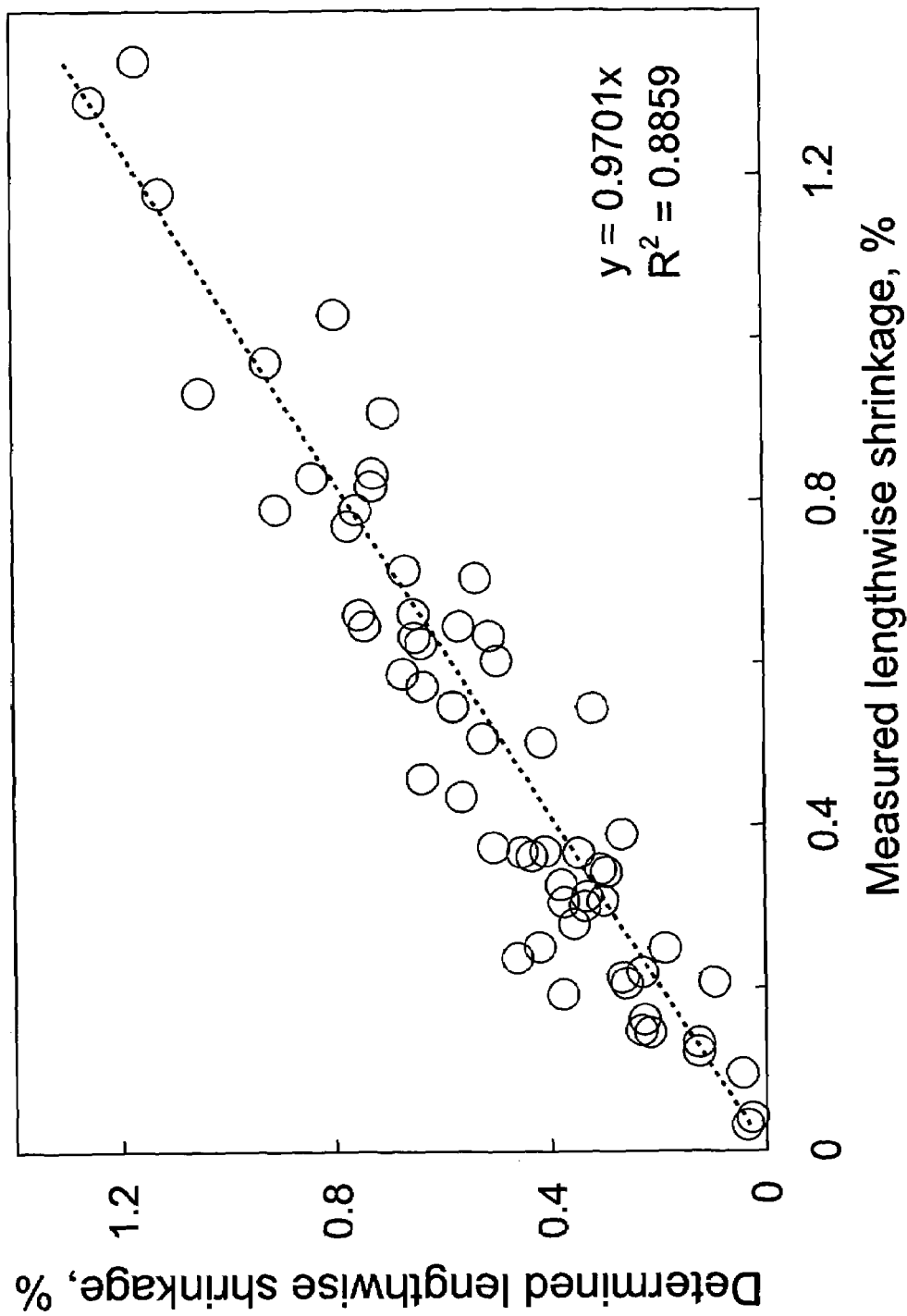
FIG. 14 is chart illustrating a comparison of actual, measured lengthwise shrinkage and determined lengthwise shrinkage using the two factor correlation for the 64 specimens indicated by the shaded data points in FIG. 11.

With the two-variable correlation as a model, a lengthwise shrinkage valuation for each specimen was quantitatively determined from the sound velocity measurements and chemical composition measurements for each specimen, and the results were compared to the actual, measured lengthwise shrinkage values previously obtained. The results of the comparison are shown in FIG. 14. A comparison of FIGS. 13 and 14 shows that using chemical composition data, such as galactan content, together with sound velocity data resulted in a significant improvement to the quantitatively determined lengthwise shrinkage valuations, as compared to using sound velocity alone.

EXAMPLE 2

Figure 15:
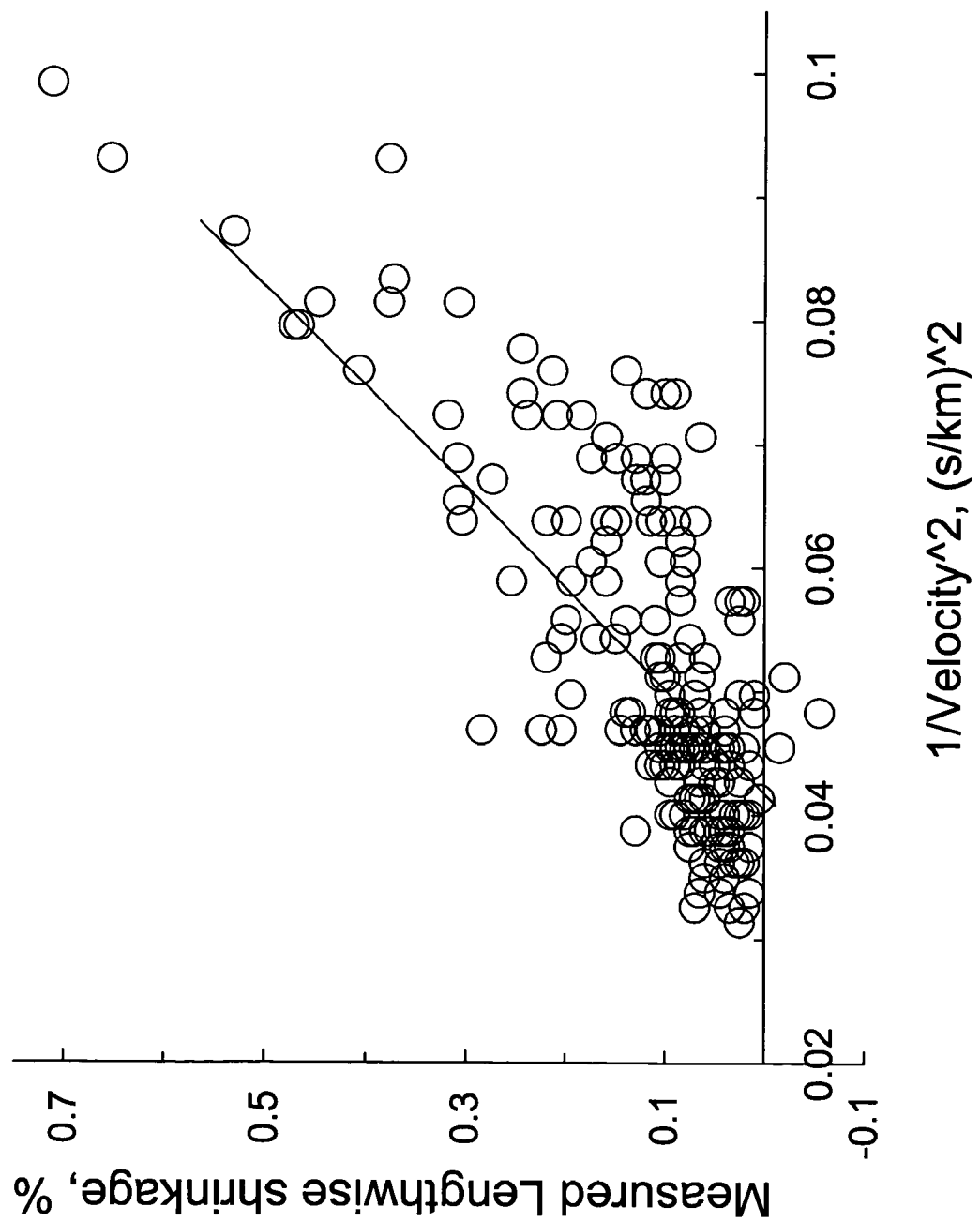
FIG. 15 is a chart illustrating the correlation between sound velocity and measured lengthwise shrinkage of multiple 1-foot-long shrinkage specimens of moldings grade lumber.

In another example, 16-ft. lengths of 5/4×6 moldings grade lumber were ripped into 1.25"-wide test strips. Eighteen such strips were subsequently brought to moisture equilibrium at 90% RH and 20% RH in order to determine the change in warp, such as bow, between the two moisture conditions. At the 20% RH equilibrium moisture condition, sound velocities were measured on both the top and bottom faces of each strip, along 1-ft. spans parallel to the strip, and repeated every foot along the strip's length. Six of the strips were each cross-cut into sixteen 1-foot lengths and was further ripped into two 1-foot-long shrinkage specimens, one from the top face and one from the bottom face of the parent strip. The length of each specimen was then measured between equilibrium moisture contents at 20% RH and 90% RH in order to determine lengthwise shrinkage. FIG. 15 shows the relationship or correlation between measured lengthwise shrinkage and sound velocity (which was measured while each specimen was still part of its parent strip and assembled into a sound velocity profile).

Figure 16:
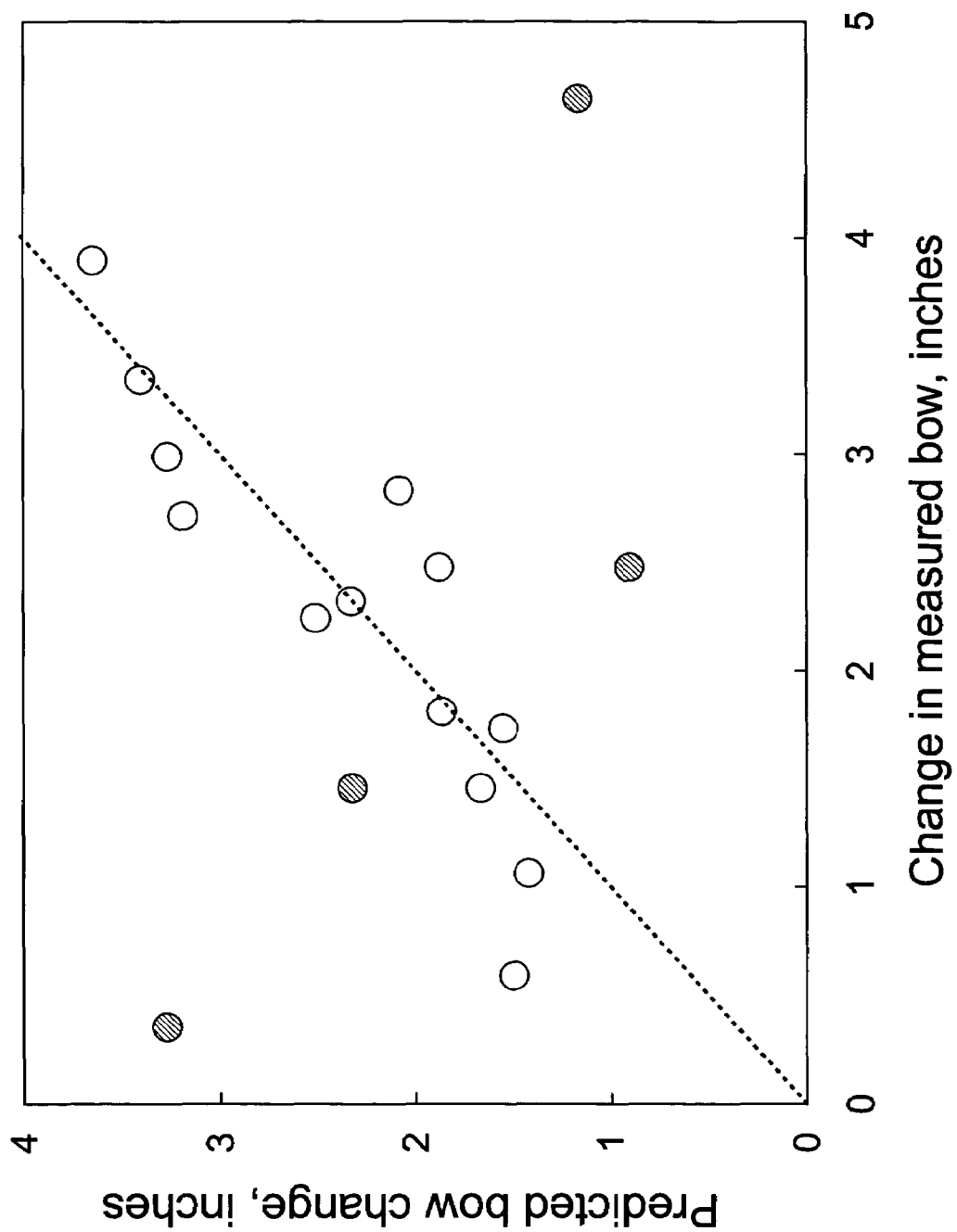
FIG. 16 is a chart illustrating a comparison of predicted bow change versus measured bow change for 18 strips of moldings grade lumber.

Next, the sound velocity profile of each of the 18 strips was converted to a lengthwise shrinkage map using the empirical relationship between shrinkage and sound velocity indicated by the solid line in FIG. 15. The resulting lengthwise shrinkage map was then used to predict the change in warp, such as bow, between the 90% RH and 20% RH equilibrium-moisture conditions using a finite element model, such as DIMENS. FIG. 16 compares the predicted warp change determined by DIMENS based on the quantified lengthwise shrinkage map to the measured (i.e. actual) warp change for the strips.

Figure 17:
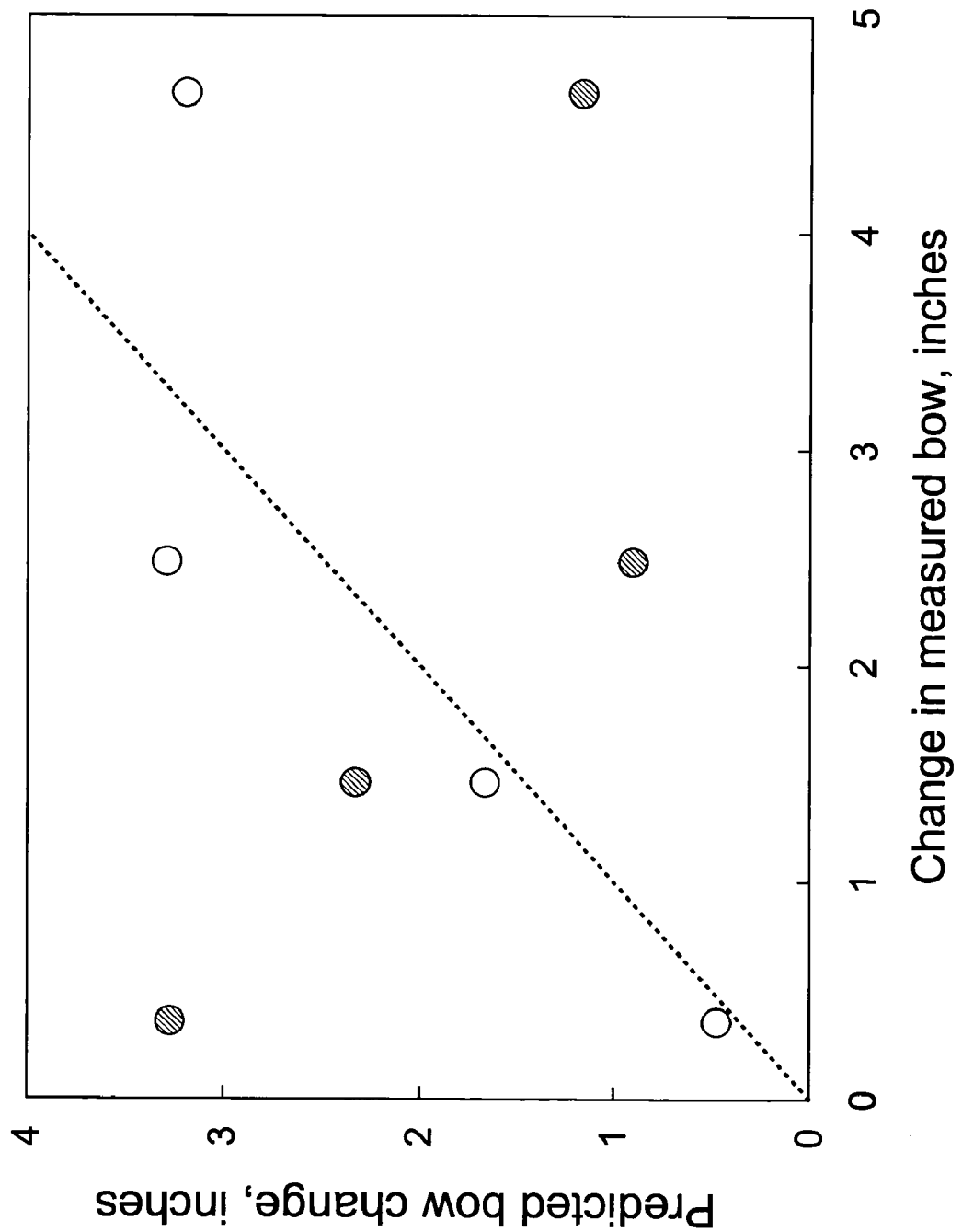
FIG. 17 is a chart illustrating the bow change predicted using both measured shrinkage values and the shrinkage valuation derived from sound velocity measurements (shown by the shaded data points) versus measured bow change for the strips indicated by the shaded data points in FIG. 16.

Four strips with poorer agreement between predicted and measured warp change (those corresponding to the shaded data points in FIG. 16) were selected for further study. Warp change in these strips was also predicted using the measured shrinkage values for those strips. The warp change predicted using measured shrinkage values and the change predicted using sound velocity-derived shrinkage valuations were compared to the actual, measured warp change in FIG. 17, which shows that for these four strips, predictions based on measured shrinkage values are substantially more accurate (the shaded points in FIG. 17 indicate the predicted warp change using sound velocity).

Figure 18:
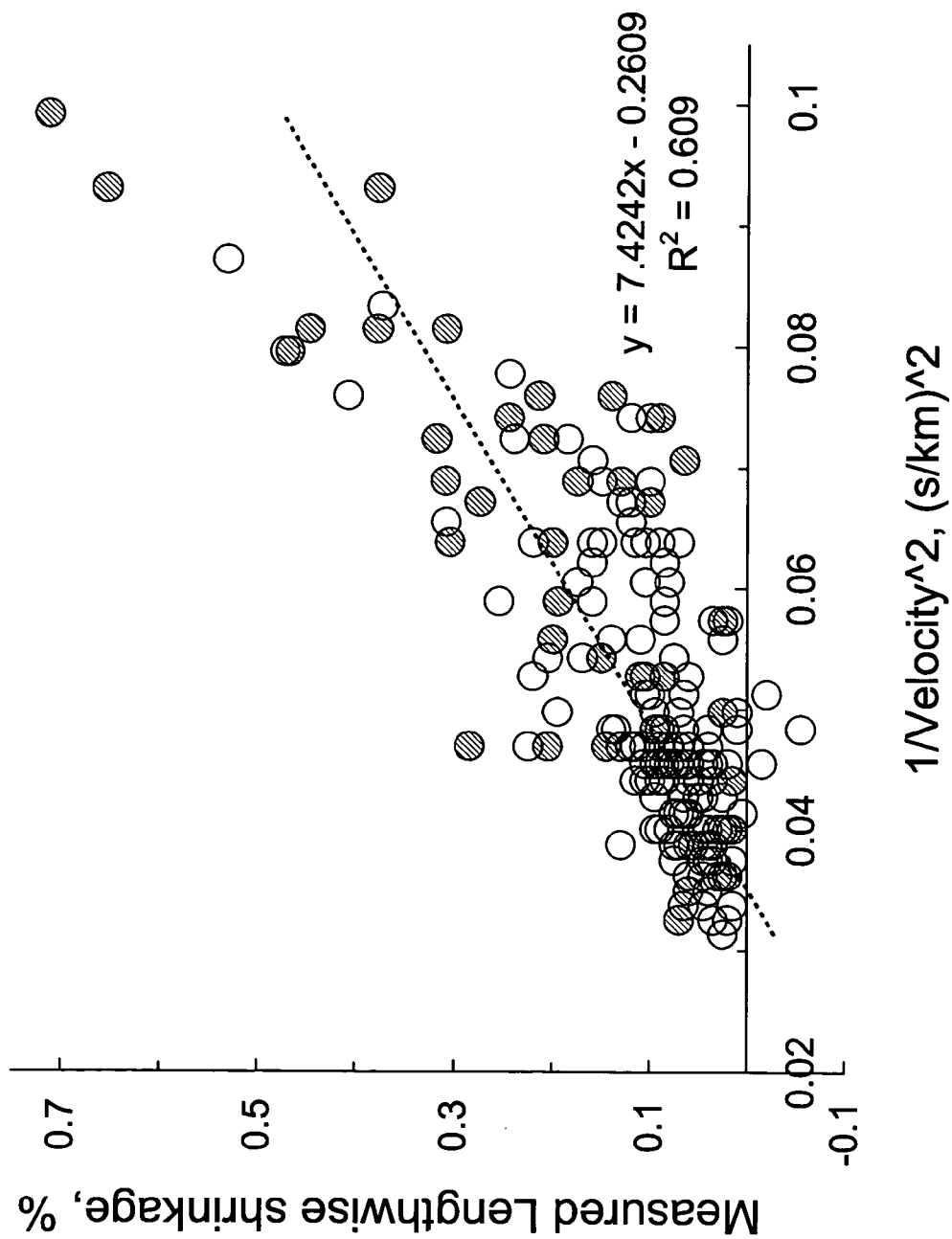
FIG. 18 is a chart illustrating the correlation between actual, measured lengthwise shrinkage and sound velocity for 43 specimens (shown by the shaded data points) created from the strips indicated by the shaded data points in FIG. 16.
Figure 19:
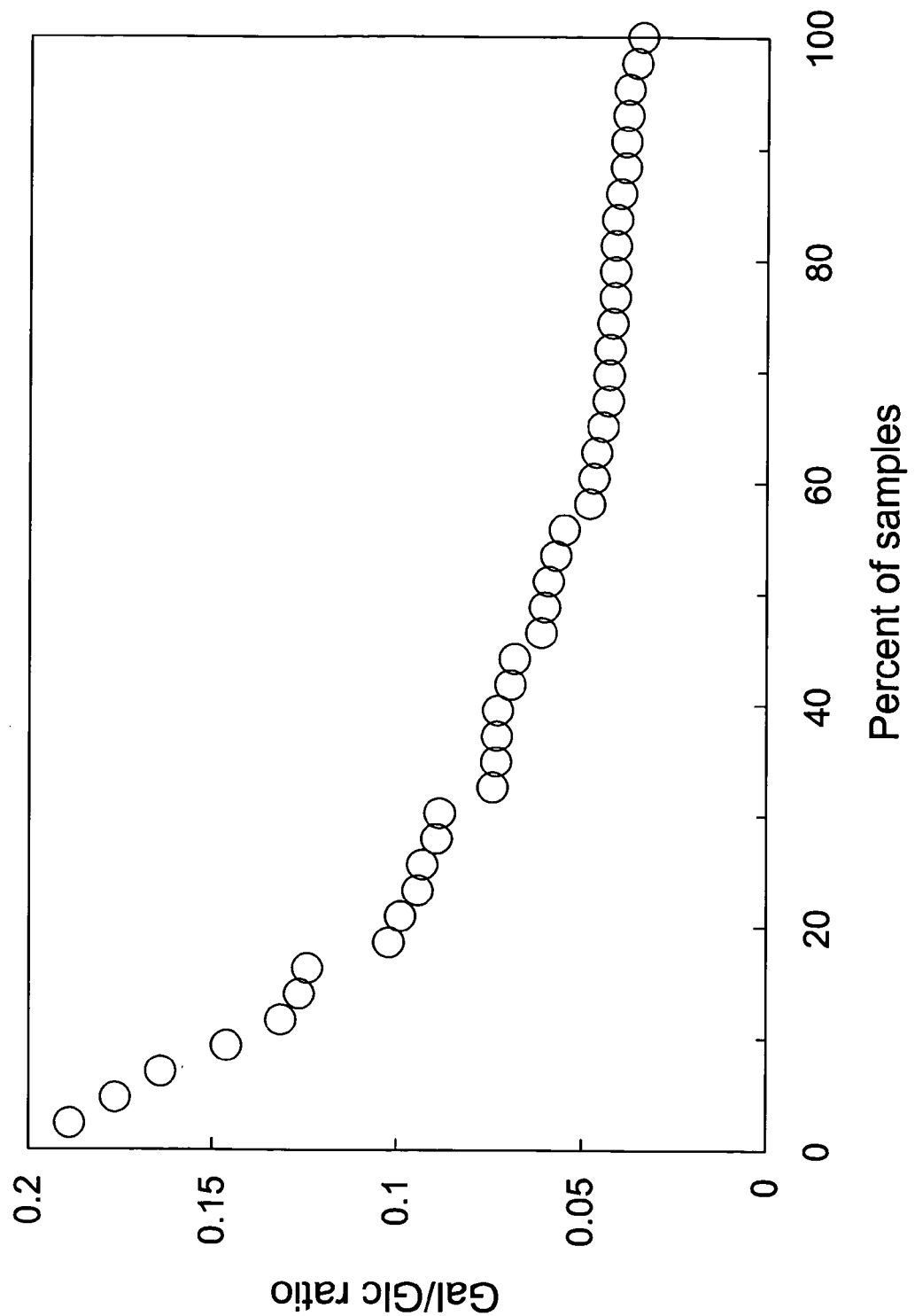
FIG. 19 is a chart illustrating the galactan content of the 43 specimens indicated by the shaded data points in FIG. 18.
Figure 20:
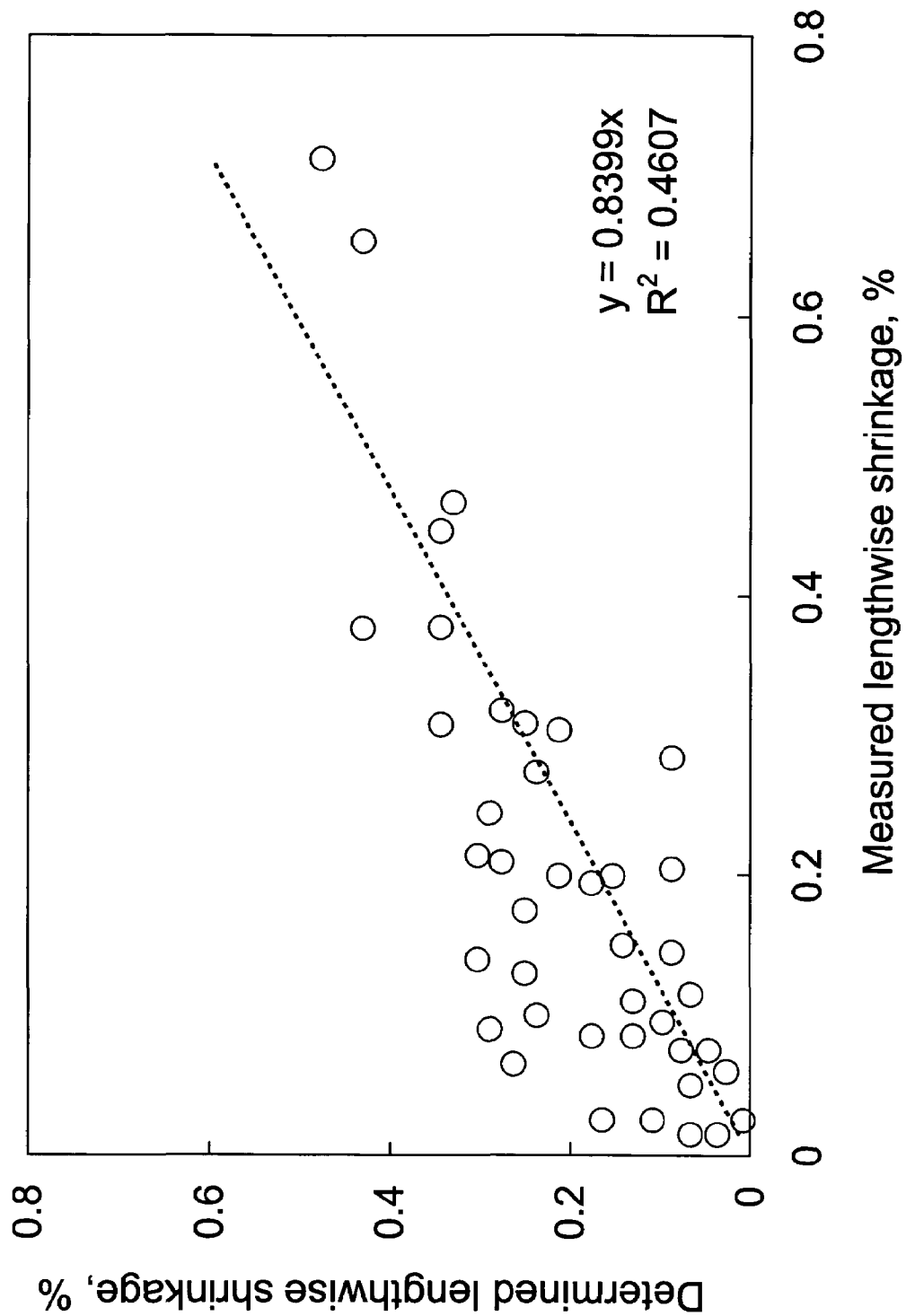
FIG. 20 is a chart illustrating the comparison of actual, measured lengthwise shrinkage and determined lengthwise shrinkage using the correlation shown in FIG. 15 for the 43 specimens indicated by the shaded data points in FIG. 18.
Figure 21:
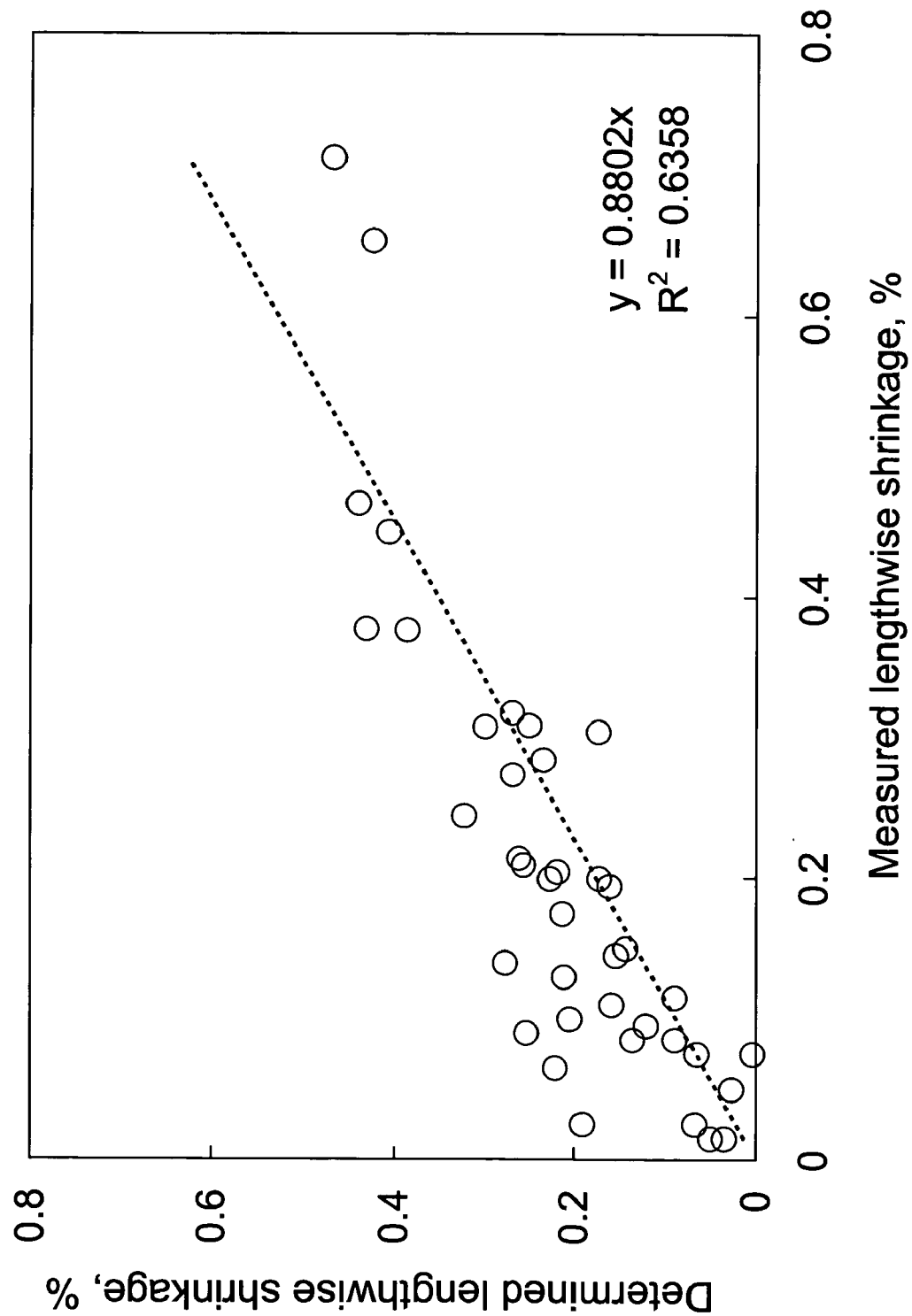
FIG. 21 is chart illustrating a comparison of actual, measured lengthwise shrinkage and determined lengthwise shrinkage using the two factor correlation for the 43 specimens indicated by the shaded data points in FIG. 18.

Next, the chemical composition of the selected subset of the specimens was obtained. Specifically, the galactan content was measured for a 43-specimen subset of the shrinkage specimens (indicated by the shaded points in FIG. 18). The distribution of galactan values among these specimens is displayed in FIG. 19. For these 43 specimens, the single-variable least-squares correlation between lengthwise shrinkage and sound velocity (previously obtained) includes an $R^2$ value of 0.61, and is represented by the broken line in FIG. 18. Using that correlation as a model, a lengthwise shrinkage valuation was calculated from the sound velocity measurement for each specimen, and the results were compared to the actual measured shrinkage values of each specimen previously obtained. Results of this comparison are shown in FIG. 20. For the same 43 specimens, a two-variable least-squares correlation between lengthwise shrinkage and both sound velocity and chemical composition ratio was generated, which resulted in an $R^2$ value of 0.71. With the two-variable correlation as a model, a lengthwise shrinkage valuation was calculated from the sound velocity and chemical composition ratio for each specimen, and the results were compared to the actual, measured shrinkage values previously obtained. Results of this comparison are shown in FIG. 21. A comparison of FIGS. 20 and 21 shows once again that using galactan information together with sound velocity data improved the shrinkage valuation, as compared to using sound velocity alone.

B. Acoustic Energy

Ultrasound is one type of acoustic energy, having a frequency range of from about ten kHz to about several megahertz, that can be used to practice the present invention. Acoustic energy also includes frequency ranges other than in the ultrasound range. For example, stress waves, having a frequency range of from about 100 Hz to the ultrasound range, also can be used to practice the present invention. Generally, any acoustic energy having a wavelength less than that of the separation distance between two measuring locations can be used to practice the present invention.

Ultrasound velocities may be measured in a variety of ways. A working embodiment of the present invention employs ultrasound pulses. An ultrasound velocity can be quantified by determining the transmission speed (i.e. the speed at which the pulse is transmitted through the wood) and the direction vector of the ultrasound pulse. Ultrasound velocity can be measured based on one ultrasound pulse or plural ultrasound pulses.

The use of acoustic energy is not limited to such devices, however. A person of ordinary skill in the art will realize that other sounding or resonating devices, or other frequencies may be utilized, so long as the acoustic signal may properly propagate through the wood. For example, the commercially available Sylvatest™ apparatus employs acoustic signals in the upper end of the audible range of sound (about 14 kHz). In fact, any device which causes an acoustic signal to propagate through the wood may be used in the present invention, including acoustic signals generated during harvesting, milling, or manufacturing, such as by a saw, planer, or sander.

C. Chemical Composition

Each wood product may be analyzed for sugar content by a technique called anion exchange chromatography, using a water/sodium hydroxide/sodium acetate gradient. Generally described, sugars at pH values >12 are anions which can be detected by electrochemical pulsed amperometry. Each sugar content measurement was quantified by peak area after calibrating with appropriate standards.

Pulp or wood samples were ground with a Wiley mill, dried in a vacuum oven overnight at 50° C. and 125 mm Hg. 50–100 mg samples are weighed to +0.0003 g accuracy, and then digested in 72% $H_2SO_4$ in a water bath at 30° C. for 90 minutes, diluted, and subjected to secondary digestion by autoclave at 14–16 psi (95–105 kPa) and >260° F. (127° C.).

Four different dilutions of standard solutions containing arabinose, galactose, glucose, xylose and mannose are autoclaved concurrently for a four-point standard curve. A standard amount of a known concentration of fucose is added to samples and standards before autoclaving, and areas for the sugar analytes are normalized with this data before calculating the concentration of sugars.

Anion exchange chromatography is then performed on each sample with a Dionex CarboPac PA-1 (P/N 35391), with a guard column of the same packing material in line before it. The chromatography system consists of a Dionex GP50 multisolvent pump, an ED40 pulsed amperometric detector, and an AS50 automatic injector with a column oven maintained at 23° C. A postcolumn solvent addition pump adds 300 mM NaOH at a rate of 0.5 mL/min.

The solvent flow at 1.0 mL/min. is a step gradient with 100% water to (17.5 min) followed by a wash of 200 mM NaOH and 150 mM sodium acetate to (28.5 min) and re-equilibration with 100% water (to 38 min). Retention times of the sugar analytes are shown in TABLE 1.

TABLE 1

| | |
|---|---|
| Fucose | 4.0 min |
| Arabinose | 7.3 min |
| Galactose | 8.3 min |
| Glucose | 9.8 min |
| Xylose | 12.1 min |
| Mannose | 13.3 min |

Results were reported as weight percents based on the dry weight of the oven-dried samples. The initial calculations give weight percents for monomeric sugars, and are adjusted with the appropriate multiplier (0.88 for the pentoses arabinose and xylose; 0.9 for the hexoses glucose, mannose and galactose) for weight percents as polymers.

D. Terms and Phrases

The following definitions are provided for certain terms and phrases used in this application. These definitions are provided solely for convenience, and should not be construed to provide a meaning having a scope less than would be understood by a person of ordinary skill in the art.

Lengthwise shrinkage is the shrinkage a particular segment of wood undergoes during drying. There is an important distinction between longitudinal and lengthwise shrinkage. Longitudinal shrinkage is defined to be shrinkage along the axis of the wood fibers. Lengthwise shrinkage parallels the length axis of the piece, an axis of measurement that may or may not be precisely parallel to the fiber direction. Unless the grain angle is zero degrees with respect to a lengthwise shrinkage measurement, lengthwise shrinkage are differentiated from longitudinal shrinkage. For small grain angles, the difference between lengthwise and longitudinal shrinkage will be small.

Modulus of elasticity (MOE) is a solid property defined to be the ratio of stress-to-strain below the material's elastic limit obtained from a uniaxial test or a bending test.

Determining warp potential depends on analyzing lengthwise shrinkage. Such patterns can be determined by measuring absolute shrinkage or from relative shrinkage patterns. Determining warp potential of wood does not require measurement of absolute shrinkage, so long as the relative shrinkage pattern can be assessed. For example, a piece of lumber could have an absolute lengthwise shrinkage at a first edge of 1.1% and a lengthwise shrinkage at a second edge of 1.2%. The relative shrinkage pattern would be 0.1%. All other pieces having the identical relative shrinkage pattern would have the same magnitude of distortion, such as another piece having an absolute lengthwise shrinkage at a first edge of 2.4% and a lengthwise shrinkage at a second edge of 2.5%.

Acoustical energy and chemical composition data can be measured at particular "measuring locations" along the wood. A measuring location is understood to be a location on or within the wood where a lengthwise shrinkage is measured. For example, working embodiments of the invention measured lengthwise shrinkage in part by using ultrasound velocity. Ultrasound velocity can be measured by sending an ultrasound pulse through wood from a first transducer to a second transducer. In such an embodiment, the measuring location would be the segment of wood located substantially around and between the transducers comprising the path of the ultrasound pulse.

Measuring locations may be separated by a predetermined distance. Working embodiments employed measuring locations spaced along one or both edges of a board by a predetermined distance of from about 12 to about 96 inches, more typically from about 12 to about 48 inches. Still other alternative embodiments use a predetermined distance of about a foot for separating measuring locations along the lengthwise span of the board.

Separation distance can be determined for a particular application by considering factors such as the spatial dimensions of the wood being studied, type of wood (e.g. hemlock, Loblolly pine, etc.), and methods used to measure lengthwise shrinkage. Not every measuring location needs to be separated by the same predetermined distance, and predetermined distances may vary along the axes of the wood. For example, measuring locations may be spaced every foot along the length of the wood while spaced approximately every 1.5 inches across the width of the wood. Moreover, one pair of measuring locations might be separated along the edge of a board by a first distance that is the same, substantially the same as, greater than, or less than a second separation distance between a second pair of measuring locations. As a general rule, working embodiments have established measuring locations along a width axis by dividing the width by an integer of from about 3 to about 6, typically about 5, and the length axis by an integer of from about 10 to about 15, typically about 12.

Working embodiments of the invention employ "nondestructive" methods for obtaining wood product measurements. For example, ultrasound propagation measurements were used in part to determine lengthwise shrinkage in a wood product. "Nondestructive" means that the wood product used is not significantly harmed or damaged and the piece is not significantly materially altered by the specific measuring techniques employed. For example, in working embodiments of the present invention, lengthwise shrinkage was established in part by using acoustic energy transmission speeds or velocities, such as ultrasound velocity. No material was removed from the wood product studied and the wood product was not damaged by obtaining the sound velocity measurements.

E. Automation of Method

Determining lengthwise shrinkage may be done by computer, in whole or in part. Working embodiments may use one or more computers to measure ultrasound velocities and compute lengthwise shrinkage from the sound velocity and chemical composition data. Alternative embodiments may employ computers to determine lengthwise shrinkage by processing previously obtained data values indicative of reactive forces, such as sound velocities, and data values indicative of motive forces, such as chemical composition data, for a piece of wood (e.g., data supplied by a third party).

While the preferred embodiments of the invention have been illustrated and described, it will be appreciated that various changes can be made therein without departing from the spirit and scope of the invention. For example, it is believed that the methods disclosed herein work equally well on green wood and dry wood. Additionally, it is believed that the methods disclosed herein work equally well on all types of warp, including crook, bow, and cup. In determining cup potential, it will be appreciated that rather than measuring lengthwise shrinkage, such embodiments employ measurements of transverse shrinkage.

The embodiments of the invention in which an exclusive property or privilege is claimed are defined as follows:

1. A method for quantifying at least one lengthwise shrinkage of a wood product, comprising:

obtaining at least one first data value indicative of a reactive force component to lengthwise shrinkage, the first data value obtained at a measuring location along the wood product;

obtaining at least one second data value indicative of a motive force component to lengthwise shrinkage wherein the motive force component to lengthwise shrinkage is chemical composition, the second data value obtained at the measuring location along the wood product wherein the second data value is a hemicellulose content measurement; and determining lengthwise shrinkage of the wood product based on the first and second data values.

2. The method of claim 1, wherein the reactive force component to lengthwise shrinkage is stiffness.

3. The method of claim 2, wherein the first data value is a modulus of elasticity measurement.

4. The method according to claim 2, wherein the first data value is an acoustic energy measurement.

5. The method of claim 4, wherein the acoustic energy measurement is a sound velocity measurement.

6. The method of claim 1, wherein obtaining a first data value indicative of a reactive force component to lengthwise shrinkage includes:

sending an ultrasound pulse through the wood product; and measuring the transmission speed of the ultrasound pulse through the wood product.

7. The method of claim 1, wherein obtaining a first data value indicative of a reactive force component to lengthwise shrinkage includes obtaining the first data value from a third party.

8. The method of claim 1, wherein the at least one first data value is a plurality of first data values and the at least one second data value is a plurality of second data values.

9. The method of claim 1, wherein the wood product is selected from a group consisting of standing trees, raw logs, processed logs, processed lumber, manufactured wood products, and engineered wood products.

10. The method of claim 1, wherein the second data value is a galactan content measurement of the hemicellulose content.

11. The method of claim 1, wherein the second data value represents a ratio of galactan to glucan of the wood product.

12. The method of claim 1, wherein obtaining the at least one second data value indicative of a motive force component to lengthwise shrinkage includes:

a) obtaining a sample of the wood product at the measuring location; and b) analyzing the sample of the wood product.

13. The method of claim 12, wherein analyzing the sample of the wood product includes conducting anion exchange chromatography on the sample.

14. The method of claim 1, wherein the second data value indicative of a motive force component of lengthwise shrinkage is obtained by anion exchange chromatography.

15. The method of claim 1, wherein determining the lengthwise shrinkage includes a) obtaining a correlation between lengthwise shrinkage and both the reactive force component to lengthwise shrinkage and the motive force component to lengthwise shrinkage for the wood product;

b) calculating the lengthwise shrinkage by converting the first and second data values with the obtained correlation.

16. The method of claim 1, wherein plural measuring locations are located along the wood product.

17. The method of claim 16, wherein at least two measuring locations are separated by a predetermined distance.

18. The method of claim 17, wherein a first or second data value is obtained at the at least two measuring locations.

19. The method according to claim 1, wherein the at least one first data value is a plurality of first data values at a plurality of measuring locations along the wood product and the at least one second data value is a plurality of second data values at the plurality of measuring locations along the wood product, and wherein determining lengthwise shrinkage includes determining the lengthwise shrinkage of the wood product at each of the plurality of measuring locations.

20. A method for quantifying lengthwise shrinkage of wood products, comprising:

obtaining a wood product;

obtaining a sound velocity measurement from the wood product at a first measuring location;

obtaining a galactan measurement from a wood product at the first measuring location; and determining lengthwise shrinkage of the wood product based on the sound velocity measurement and the galactan measurement.

21. The method of claim 20, wherein the galactan measurement is a galactan to glucan ratio.

* * * * *